United States Patent [19]
Kisilevsky et al.

[11] Patent Number: 5,840,294
[45] Date of Patent: *Nov. 24, 1998

[54] METHOD FOR TREATING AMYLOIDOSIS

[75] Inventors: Robert Kisilevsky; Walter Szarek; Donald Weaver, all of Kingston, Canada

[73] Assignee: Queen's University at Kingston, Kingston, Canada

[*] Notice: The term of this patent shall not extend beyond the expiration date of Pat. No. 5,463,562.

[21] Appl. No.: 542,997

[22] Filed: Oct. 13, 1995

Related U.S. Application Data

[63] Continuation-in-part of Ser. No. 463,548, Jun. 5, 1995, which is a continuation-in-part of Ser. No. 403,230, Mar. 15, 1995, Pat. No. 5,643,562, which is a continuation-in-part of Ser. No. 315,391, Sep. 29, 1994, abandoned, which is a continuation-in-part of Ser. No. 219,798, Mar. 29, 1994, abandoned, which is a continuation-in-part of Ser. No. 37,844, Mar. 29, 1993, abandoned.

[51] Int. Cl.$^6$ .................. A61K 31/74; A61K 31/785; A61K 31/795; A61F 2/02
[52] U.S. Cl. .................. 424/78.31; 424/78.35; 424/423; 424/427; 424/430; 424/434; 424/436; 424/441; 424/450; 514/772.4; 526/286; 526/287
[58] Field of Search .................. 424/450, 78.31, 424/78.35, 423, 427, 430, 434, 436, 441; 514/772.4; 526/286, 287

[56] References Cited

U.S. PATENT DOCUMENTS

| | | | |
|---|---|---|---|
| 5,242,932 | 9/1993 | Gandy et al. | 514/313 |
| 5,276,059 | 1/1994 | Caughey et al. | 514/647 |
| 5,385,915 | 1/1995 | Buxbaum et al. | 514/313 |

FOREIGN PATENT DOCUMENTS 0 464 759 A2  1/1992  European Pat. Off. .

OTHER PUBLICATIONS

Caughey, B. and Raymond, G. J., (1993), "Sulfated Polyanion Inhibition of Scrapie-Associated PrP Accumulation in Cultured Cells", *Journal of Virology*, vol. 67, No. 2, pp. 643–650.

Travis, (1993), "New Piece in Alzheimer's Puzzle", *Science*, vol. 261, pp. 828–829.

Kisilevsky et al., (1992), "A Critical Analysis of Postulated Pathogenetic Mechanisms in Amyloidogenesis", *Critical Reviews in Clinical Laboratory Sciences*, vol. 29, No. 1, pp. 59–82.

Young et al., (1992), "Localization of the Basement Membrane Heparan Sulfate Proteoglycan in Islet Amyloid Deposits in Type II Diabetes Mellitus", *Arch. Pathol. Lab. Med.*, vol. 116, pp. 951–954.

Dow et al., (1992), "Effects of 4-deoxy-L-threo-pentose, a novel carbohydrate, on neural cell proteoglycan synthesis and function", *Biochimica et Biophysica Acta*, vol. 1156, pp. 7–14.

Narindrasorasak et al., (1992), "Characterization of High Affinity Binding between Laminin and Alzheimer's Disease Amyloid Precursor Proteins", *Laboratory Investigation*, vol. 67, No. 5, pp. 643–652.

(List continued on next page.)

*Primary Examiner*—Carlos Azpuru
*Attorney, Agent, or Firm*—Lahive & Cockfield, LLP

[57] ABSTRACT

Therapeutic compounds and methods for inhibiting amyloid deposition in a subject, whatever its clinical setting, are described. Amyloid deposition is inhibited by the administration to a subject of an effective amount of a therapeutic compound comprising an anionic group and a carrier molecule, or a pharmaceutically acceptable salt thereof, such that an interaction between an amyloidogenic protein and a basement membrane constituent is inhibited. Preferred anionic groups are sulfonates and sulfates. Preferred carrier molecules include carbohydrates, polymers, peptides, peptide derivatives, aliphatic groups, alicyclic groups, heterocyclic groups, aromatic groups and combinations thereof.

66 Claims, 12 Drawing Sheets

OTHER PUBLICATIONS

Small et al., (1992), "Association and Release of the Amyloid Protein Precursor of Alzheimer's Disease from Chick Brain Extracellular Matrix", *The Journal of Neuroscience*, vol. 12, No. 11, pp. 4143–4150.

Fraser et al., (1992), "Effects of Sulfate Ions on ALzheimer–beta/A4 Peptide Assemblies—Implications for Amyloid Fibril–Proteoglycan Interactions", *J. Neurochem.*, vol. 59, pp. 1531–1540.

Narindrasorasak et al., (1991), "High Affinity Intereactions between the Alzheimer's β–Amyloid Precursor Proteins and the Basement Membrane Form of Heparan Sulfate Proteoglycan", *The Journal of Biological Chemistry*, vol. 266, No. 20, pp. 12878–12883.

Lyon et al., (1991), "Co–deposition of Basement Membrane Components during the Induction of murine Splenic AA Amyloid", *Laboratory Investigation*, vol. 64, No. 6, pp. 785–790.

Snow et al., (1991), "A Temporal and Ultrastructural Relationship Between Heparan Sulfate Proteoglycans and AA Amyloid in Experimental Amyloidosis", *The Journal of Histochemistry and Cytochemistry*, vol. 39, No. 10, pp. 1321–1330.

Wong et al., (1990), "Influence of Sulphate ions on the Structure of AA Amyloid Fibrils", *Scand. J. Immunol.*, vol. 32, pp. 225–232.

Kisilevsky, (1990), "Heparan Sulfate Proteoglycans in Amyloidogenesis: An Epiphenomenon, A Unique Factor, or the Tip of a More Fundamental Process?", *Laboratory Investigation*, vol. 63, No. 5, pp. 589–591.

Young et al., (1989), "The ultrastructural localization of sulfated proteoglycans is identical in the amyloids of Alzheimer's disease and AA, AL, senile cardiac and medullary carcinoma–associated amyloidosis", *Acta Neuropathol.*, vol., 78, pp. 202–209.

Brissette et al., (1989), "Differential Induction of the Serum Amyloid A Gene Family in Response to an Inflammatory Agent and to Amyloid–enhancing Factor", *The Journal of Biological Chemistry*, vol. 264, No. 32, pp. 19327–19332.

Snow et al., (1989), "Sulfated glycosaminoglycans in amyloid plaques of prion diseases", *Acta Neuropathol.*, vol. 77, pp. 337–342.

Kisilevsky, (1989), "Theme and Variations on a String of Amyloid", *Neurobiology of Aging*, vol. 10, pp. 499–500.

Kisilevsky, R. and Snow, A., (1988), "The Potential Significance of Sulphated Glycosaminoglycans as a Common Constituent of all Amyloids: or Perhaps Amyloid is not a Misnomer", *Medical Hypotheses*, vol. 26, pp. 231–236.

McCubbin et al., (1988), "Circular–dichroism studies on two murine serum amyloid A proteins", *Biochem. J.*, vol. 256, pp. 775–783.

Tape et al., (1988), "Direct Evidence for Circulating apoSAA as the Precursor of Tissue AA Amyloid Deposits", *Scand. J. Immunol.*, vol. 28, pp. 317–324.

Kisilevsky, (1987), "From arthritis to Alzheimer's disease: current concepts on the pathogenesis of amyloidosis", *Can. J. Physiol. Pharmacol.*, vol. 65, pp. 1805–1815.

Snow et al., (1987), "Sulfated Glycosaminoglycans in Alzheimer's Disease", *Human Pathology*, vol. 18, No. 5, pp. 506–510.

Snow et al., (1987), "Characterization of Tissue and Plasma Glycosaminoglycans during Experimental AA Amyloidosis and Acute Inflammation", *Laboratory Investigation*, vol. 56, No. 6, pp. 665–675.

Snow et al., (1987), "A Close Ultrastructural Relationship between Sulfated Proteoglycans and AA Amyloid Fibrils", *Laboratory Investigation*, vol. 57, No. 6, pp. 687–697.

Snow et al., (1987), "Sulfated Glycosaminoglycans: A Common Constituent of All Amyloids?", *Laboratory Investigation*, vol. 56, No. 1, pp. 120–123.

Snow, A. D. and Kisilevsky, R., (1985), "Temporal Relationship between Glycosaminoglycan Accumulation and Amyloid Deposition during Experimental Amyloidosis", *Laboratory Investigation*, vol. 53, No. 1, pp. 37–43.

Ehlers et al., (1984), "Dextran Sulphate 500 Delays and Prevents Mouse Scrapie by Impairment of Agent Replication in Spleen", *J. Gen. Virol.*, vol. 65, pp. 1325–1330.

Puchtler et al., (1983), "Application of Thiazole Dyes to Amyloid Under Conditions of Direct cotton Dyeing: Correlation of Histochemical and Chemical Data", *Histochemistry*, vol. 77, pp. 431–445.

Axelrad et al., (1982), "Further Characterization of Amyloid Enhancing Factor", *Laboratory Investigation*, vol. 47, pp. 139–146.

Leveugle, B. et al., (1994), "Binding of heparan sulfate glycosaminoglycan to β–amyloid peptide: inhibition by potentially therapeutic polysulfated compounds", *NeuroReport*, vol. 5, pp. 1389–1392.

Caughey, B. et al., (1994), "Binding of the Protease–Sensitive Form of Prion Protein PrP to Sulfated Glysocaminoglycan and Congo Red", *Journal of Virology*, vol. 68, pp. 2135–2141.

Caughey, B., (1993), "Scrapie–Associated PrP Accumulation and Its Prevention: Insights from Cell Culture", *Brit. Med. Bull.*, vol. 49, pp. 860–872.

Caughey, B., (1994), "Protease–resistant PrP accumulation and scrapie agent replication: a role for sulphated glycosaminoglycans?", *Biochem. Soc. Trans.*, vol. 22, pp. 163–167.

Caughey, B., (1994), "Scrapie–associated PrP accumulation and agent replication: effects of sulphated glycosaminoglycan analogues", *Phil. Trans. R. Soc. Lond. B*, vol. 343, pp. 399–404.

Kagan, D.Z. and Rozinova, V.N. (1974) "Inhibition of amyloidosis with Congo Red in experimental amyloidosis", *Problemy Tuberkuleza*, vol. 40, pp. 72–74. (with English translation).

Kisilevsky, R. et al., (1995), "Arresting amyloidosis in vivo using small–molecule anionic sulphonates or sulphates: implications for Alzheimer's disease", *Nature Med.* vol. 1, pp. 143–148.

XXI

XXII

XXIII

XXIV

XXV

XXVI

XXVII

XXVIII

XXIX

XXX

XXXI

XXXII

R = SO$_3$Na
XXXIII

XXXIV

XXXV

XXXVI

XXXVII

XXXVIII

XXXIX

XL

XLI

XLII

XLIII

XLIV

XLV  XLVI

XLVII

XLVIII

XLIX

L

LI

LII

LIII

LIV

LV

LVI

LVII

LVIII

LIX

LX

LXI

LXII

LXIII

LXIV

LXV

LXVI

LXVII

LXVIII

LXIX

LXX

LXXI

LXXII

LXXIII

LXXIV

LXXV

LXXVI

LXXVII

METHOD FOR TREATING AMYLOIDOSIS

RELATED APPLICATIONS

This application is a continuation-in-part of application Ser. No. 08/463,548 filed Jun. 5, 1995, which is a continuation-in-part of application Ser. No. 08/403,230, filed Mar. 15, 1995, now U.S. Pat. No. 5,643,562 which is a continuation-in-part of application Ser. No. 08/315,391, filed Sep. 29, 1994, now abandoned, which is a continuation-in-part of application Ser. No. 08/219,798, filed Mar. 29, 1994, now abandoned, which is a continuation-in-part of application Ser. No. 08/037,844 filed Mar. 29, 1993, now abandoned, the contents of all of which are incorporated herein by reference.

BACKGROUND OF INVENTION

Amyloidosis refers to a pathological condition characterized by the presence of amyloid. Amyloid is a generic term referring to a group of diverse but specific extracellular protein deposits which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common x-ray diffraction and infrared spectra.

Amyloidosis can be classified clinically as primary, secondary, familial and/or isolated. Primary amyloidosis appears de novo without any preceding disorder. Secondary amyloidosis is that form which appears as a complication of a previously existing disorder. Familial amyloidosis is a genetically inherited form found in particular geographic populations. Isolated forms of amyloidosis are those that tend to involve a single organ system. Different amyloids are also characterized by the type of protein present in the deposit. For example, neurodegenerative diseases such as scrapie, bovine spongiform encephalitis, Creutzfeldt-Jakob disease and the like are characterized by the appearance and accumulation of a protease-resistant form of a prion protein (referred to as AScr or PrP-27) in the central nervous system. Similarly, Alzheimer's disease, another neurodegenerative disorder, is characterized by congophilic angiopathy, neuritic plaques and neurofibrillary tangles, all of which have the characteristics of amyloids. In this case, the plaques and blood vessel amyloid is formed by the beta protein. Other systemic diseases such as adult-onset diabetes, complications of long-term hemodialysis and sequelae of long-standing inflammation or plasma cell dyscrasias are characterized by the accumulation of amyloids systemically. In each of these cases, a different amyloidogenic protein is involved in amyloid deposition.

Once these amyloids have formed, there is no known therapy or treatment which significantly dissolves the deposits in situ which is widely accepted.

SUMMARY OF THE INVENTION

This invention provides methods and compositions which are useful in the treatment of amyloidosis. The methods of the invention involve administering to a subject a therapeutic compound which inhibits amyloid deposition. Accordingly, the compositions and methods of the invention are useful for inhibiting amyloidosis in disorders in which amyloid deposition occurs. The methods of the invention can be used therapeutically to treat amyloidosis or can be used prophylactically in a subject susceptible to amyloidosis. The methods of the invention are based, at least in part, on inhibiting an interaction between an amyloidogenic protein and a constituent of basement membrane to inhibit amyloid deposition. The constituent of basement membrane is a glycoprotein or proteoglycan, preferably heparan sulfate proteoglycan. A therapeutic compound used in the method of the invention can interfere with binding of a basement membrane constituent to a target binding site on an amyloidogenic protein, thereby inhibiting amyloid deposition.

In one embodiment, the method of the invention involves administering to a subject a therapeutic compound having at least one anionic group covalently attached to a carrier molecule which is capable of inhibiting an interaction between an amyloidogenic protein and a glycoprotein or proteoglycan constituent of a basement membrane to inhibit amyloid deposition. In one embodiment, the anionic group covalently attached to the carrier molecule is a sulfonate group. Accordingly, the therapeutic compound can have the formula:

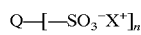

wherein Q is a carrier molecule; $X^+$ is a cationic group; and n is an integer. In another embodiment, the anionic group is a sulfate group. Accordingly, the therapeutic compound can have the formula:

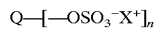

wherein Q is a carrier molecule; $X^+$ is a cationic group; and n is an integer. Carrier molecules which can be used include carbohydrates, polymers, peptides, peptide derivatives, aliphatic groups, alicyclic groups, heterocyclic groups, aromatic groups and combinations thereof. Preferred therapeutic compounds for use in the invention include poly (vinylsulfonic acid), ethanesulfonic acid, sucrose octasulfate, 1,2-ethanediol disulfuric acid, 1,2-ethanedisulfonic acid, 1,3-propanediol disulfuric acid, 1,3-propanedisulfonic acid, 1,4-butanediol disulfuric acid, 1,4-butanedisulfonic acid, 1,5-pentanedisulfonic acid, taurine, 3-(N-morpholino)propanesulfonic acid, tetrahydrothiophene-1,1-dioxide-3,4-disulfonic acid, 4-hydroxybutane-1-sulfonic acid, or pharmaceutically acceptable salts thereof. Other preferred therapeutic compounds for use in the invention include 1-butanesulfonic acid, 1-decanesulfonic acid, 2-propanesulfonic acid, 3-pentanesulfonic acid, 4-heptanesulfonic acid, and pharmaceutically acceptable salts thereof. In other preferred embodiments, the therapeutic compound is 1,7-dihydroxy-4-heptanesulfonic acid, or a pharmaceutically acceptable salt thereof. In yet other preferred embodiments, the therapeutic compound is selected from the group consisting of 2-hydroxymethyl-1,3-propanediol disulfuric acid, 2-hydroxymethyl-2-methyl-1,3-propanediol disulfuric acid, 1,3-cyclohexanediol disulfuric acid, and pharmaceutically acceptable salts thereof. In still other preferred embodiments, the therapeutic compound is 2,3,4,3',4'-sucrose pentasulfuric acid, or a pharmaceutically acceptable salt thereof. In yet other preferred embodiments, the therapeutic compound is selected from the group consisting of 2-hydroxyethylsulfuric acid sulfuric acid, 3-hydroxypropylsulfamic acid sulfuric acid, and pharmaceutically acceptable salts thereof. In yet other preferred embodiments, the therapeutic compound is selected from the group consisting of 1,3,5,7-heptane tetrasulfuric acid and 1,3,5,7,9-nonane pentasulfuric acid, and pharmaceutically acceptable salts thereof.

In another embodiment, the anionic group is a tetrazole group. Thus, in one embodiment, the invention features a method for inhibiting amyloid deposition in a subject comprising administering to the subject an effective amount of a therapeutic compound, the therapeutic compound comprising at least one tetrazole group covalently attached to a carrier molecule, or a pharmaceutically acceptable salt thereof. In certain preferred embodiments, the therapeutic compound is selected from the group consisting of 3-(1H-tetrazol-5-yl)-9H-thioxanthen-9-one 10,10-dioxide, 5,5-dithiobis(1-phenyltetrazole), 1H-tetrazole, 5-phenyl-1H-tetrazole, and 5-(2-aminoethanoic acid)-1H-tetrazole, and pharmaceutically acceptable salts thereof.

The therapeutic compounds of the invention are administered to a subject by a route which is effective for inhibition of amyloid deposition. Suitable routes of administration include subcutaneous, intravenous and intraperitoneal injection. The therapeutic compounds of the invention have been found to be effective when administered orally. Accordingly, a preferred route of administration is oral administration. The therapeutic compounds can be administered with a pharmaceutically acceptable vehicle.

The invention further provides pharmaceutical compositions for treating amyloidosis. The pharmaceutical compositions include a therapeutic compound of the invention in an amount effective to inhibit amyloid deposition and a pharmaceutically acceptable vehicle.

DETAILED DESCRIPTION OF INVENTION

Figure 1:
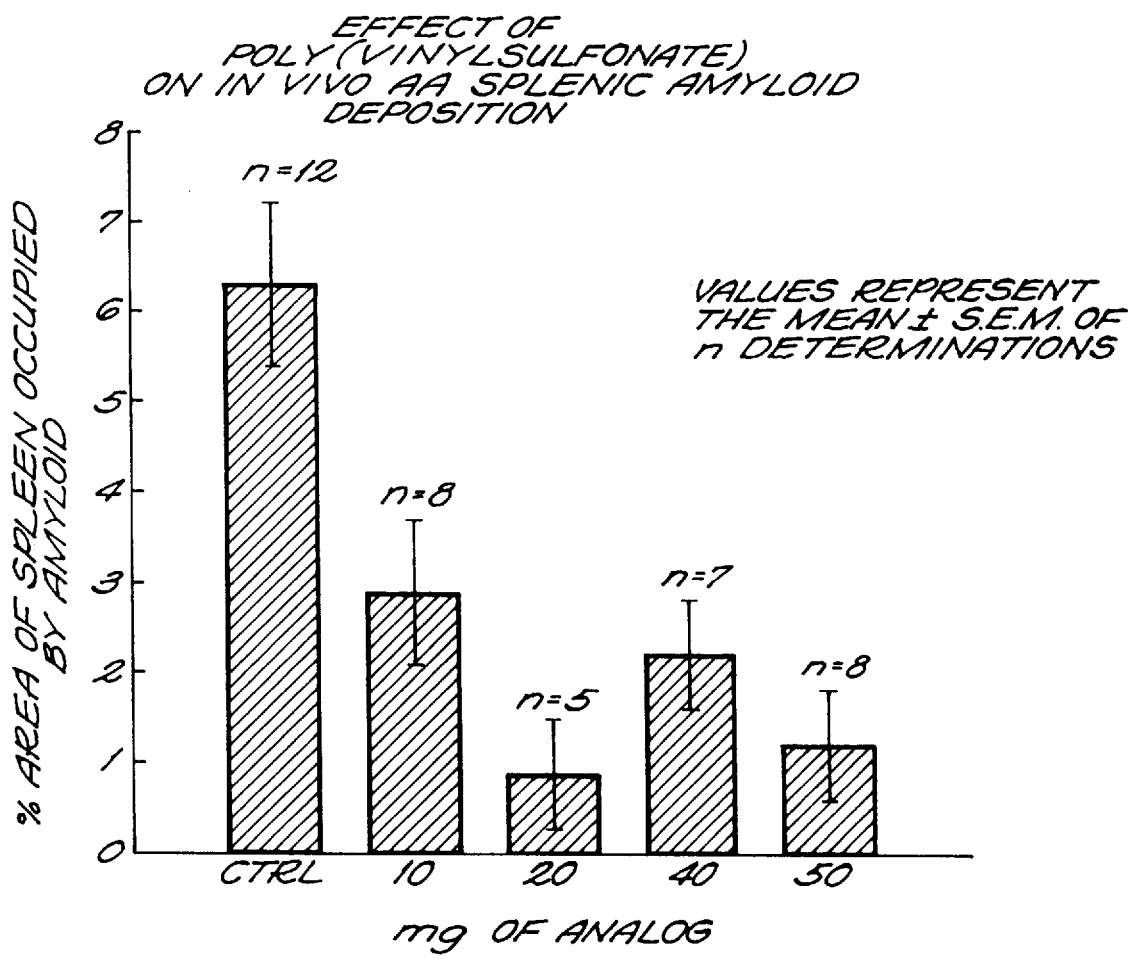
FIG. 1 is a bar graph illustrating the effect of poly(vinylsulfonate sodium salt) administered intraperitoneally on in vivo AA amyloid deposition in mouse spleen.

This invention pertains to methods and compositions useful for treating amyloidosis. The methods of the invention involve administering to a subject a therapeutic compound which inhibits amyloid deposition. "Inhibition of amyloid deposition" is intended to encompass prevention of amyloid formation, inhibition of further amyloid deposition in a subject with ongoing amyloidosis and reduction of amyloid deposits in a subject with ongoing amyloidosis. Inhibition of amyloid deposition is determined relative to an untreated subject or relative to the treated subject prior to treatment. Amyloid deposition is inhibited by inhibiting an interaction between an amyloidogenic protein and a constituent of basement membrane. "Basement membrane" refers to an extracellular matrix comprising glycoproteins and proteoglycans, including laminin, collagen type IV, fibronectin and heparan sulfate proteoglycan (HSPG). In one embodiment, amyloid deposition is inhibited by interfering with an interaction between an amyloidogenic protein and a sulfated glycosaminoglycan such as HSPG. Sulfated glycosaminoglycans are known to be present in all types of amyloids (see Snow, A. D. et al. (1987) Lab. Invest. 56:120–123) and amyloid deposition and HSPG deposition occur coincidentally in animal models of amyloidosis (see Snow, A. D. et al. (1987) Lab. Invest. 56:665–675). In the methods of the invention, molecules which have a similar structure to a sulfated glycosaminoglycan are used to inhibit an interaction between an amyloidogenic protein and basement membrane constituent. In particular, the therapeutic compounds of the invention comprise at least one sulfate group or a functional equivalent thereof, for example a sulfonic acid group or other functionally equivalent anionic group, linked to a carrier molecule. In addition to functioning as a carrier for the anionic functionality, the carrier molecule can enable the compound to traverse biological membranes and to be biodistributed without excessive or premature metabolism. Moreover, when multiple anionic functionalities are present on a carrier molecule, the carrier molecule serves to space the anionic groups in a correct geometric separation.

In one embodiment, the method of the invention includes administering to the subject an effective amount of a therapeutic compound which has at least one anionic group covalently attached to a carrier molecule. The therapeutic compound is capable of inhibiting an interaction between an amyloidogenic protein and a glycoprotein or proteoglycan constituent of a basement membrane to thus inhibit amyloid deposition. The therapeutic compound can have the formula:

$$Q-[-Y^-X^+]_n$$

wherein $Y^-$ is an anionic group at physiological pH; Q is a carrier molecule; $X^+$ is a cationic group; and n is an integer. The number of anionic groups ("n") is selected such that the biodistribution of the compound for an intended target site is not prevented while maintaining activity of the compound. For example, the number of anionic groups is not so great as to inhibit traversal of an anatomical barrier, such as a cell membrane, or entry across a physiological barrier, such as the blood-brain barrier, in situations where such properties are desired. In one embodiment, n is an integer between 1 and 10. In another embodiment, n is an integer between 3 and 8.

An anionic group of a therapeutic compound of the invention is a negatively charged moiety that, when attached to a carrier molecule, can inhibit an interaction between an amyloidogenic protein and a glycoprotein or proteoglycan constituent of a basement membrane to thus inhibit amyloid deposition. For purposes of this invention, the anionic group is negatively charged at physiological pH. Preferably, the anionic therapeutic compound mimics the structure of a sulfated proteoglycan, i.e., is a sulfated compound or a functional equivalent thereof. "Functional equivalents" of sulfates are intended to include compounds such as sulfamates as well as bioisosteres. Bioisosteres encompass both classical bioisosteric equivalents and non-classical bioisosteric equivalents. Classical and non-classical bioisosteres of sulfate groups are known in the art (see e.g. Silverman, R. B. *The Organic Chemistry of Drug Design and Drug Action*, Academic Press, Inc.:San Diego, Calif., 1992, pp.19–23). Accordingly, a therapeutic compound of the invention can comprise at least one anionic group including sulfonates, sulfates, sulfamates, phosphonates, phosphates, carboxylates, and heterocyclic groups of the following formulas:

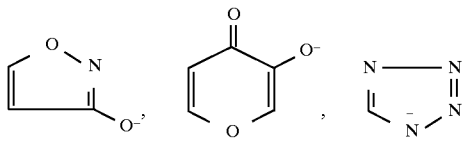

Depending on the carrier molecule, more than one anionic group can be attached thereto. When more than one anionic group is attached to a carrier molecule, the multiple anionic groups can be the same structural group (e.g., all sulfonates) or, alternatively, a combination of different anionic groups can be used (e.g., sulfonates and sulfates, etc.).

The ability of a therapeutic compound of the invention to inhibit an interaction between an amyloidogenic protein and a glycoprotein or proteoglycan constituent of a basement membrane can be assessed by an in vitro binding assay, such as that described in the Exemplification or in U.S. Pat. No. 5,164,295 by Kisilevsky et al. Briefly, a solid support such as a polystyrene microtiter plate is coated with an amyloidogenic protein (e.g., serum amyloid A protein or β-amyloid precursor protein (β-APP)) and any residual hydrophobic surfaces are blocked. The coated solid support is incubated with various concentrations of a constituent of basement membrane, preferably HSPG, either in the presence or absence of a compound to be tested. The solid support is washed extensively to remove unbound material. The binding of the basement membrane constituent (e.g., HSPG) to the amyloidogenic protein (e.g., β-APP) is then measured using an antibody directed against the basement membrane constituent which is conjugated to a detectable substance (e.g., an enzyme, such as alkaline phosphatase) by detecting the detectable substance. A compound which inhibits an interaction between an amyloidogenic protein and a glycoprotein or proteoglycan constituent of a basement membrane will reduce the amount of substance detected (e.g., will inhibit the amount of enzyme activity detected).

Preferably, a therapeutic compound of the invention interacts with a binding site for a basement membrane glycoprotein or proteoglycan in an amyloidogenic protein and thereby inhibits the binding of the amyloidogenic protein to the basement membrane constituent. Basement membrane glycoproteins and proteoglycans include laminin, collagen type IV, fibronectin and heparan sulfate proteoglycan (HSPG). In a preferred embodiment, the therapeutic compound inhibits an interaction between an amyloidogenic protein and HSPG. Consensus binding site motifs for HSPG in amyloidogenic proteins have been described (see e.g. Cardin and Weintraub (1989) *Arteriosclerosis* 9:21–32). For example, an HSPG consensus binding motif can be of the general formula X1—X2—Y—X3, wherein X1, X2 and X3 are basic amino acids (e.g., lysine or arginine) and Y is any amino acid. Modeling of the geometry of this site led to determination of the following spacing between basic amino acid residues (carboxylate to carboxylate, in Angstroms):

$X1 - X2 \quad 5.3 \pm 1.5 \text{Å}$ $X1 - X3 \quad 7.1 \pm 1.5 \text{Å}$ $X2 - X3 \quad 7.6 \pm 1.5 \text{Å}$ These values were determined using a combination of molecular mechanics and semi-empirical quantum mechanics calculations. Molecular mechanics calculations were performed using the MM2 force field equation. Semi-empirical molecular orbital calculations were performed using the AM1 Hamiltonian equation. The conformational space of the site was sampled using a combination of molecular dynamics (both high and low temperature) and Monte Carlo simulations.

Accordingly, in the therapeutic compounds of the invention, when multiple anionic groups are attached to a carrier molecule, the relative spacing of the anionic groups can be chosen such that the anionic groups (e.g., sulfonates) optimally interact with the basic residues within the HSPG binding site (thereby inhibiting interaction of HSPG with the site). For example, anionic groups can be spaced approximately $5.3 \pm 1.5$ Å, $7.1 \pm 1.5$ Å and/or $7.6 \pm 1.5$ Å apart, or appropriate multiples thereof, such that the relative spacing of the anionic groups allows for optimal interaction with a binding site for a basement membrane constituent (e.g., HSPG) in an amyloidogenic protein.

A therapeutic compound of the invention typically further comprises a counter cation (i.e., $X^+$ in the general formula: $Q—[—Y^-X^+]_n$). Cationic groups include positively charged atoms and moieties. If the cationic group is hydrogen, $H^+$, then the compound is considered an acid, e.g., ethanesulfonic acid. If hydrogen is replaced by a metal or its equivalent, the compound is a salt of the acid. Pharmaceutically acceptable salts of the therapeutic compound are within the scope of the invention. For example, $X^+$ can be a pharmaceutically acceptable alkali metal, alkaline earth, higher valency cation (e.g., aluminum salt), polycationic counter ion or ammonium. A preferred pharmaceutically acceptable salt is a sodium salt but other salts are also contemplated within their pharmaceutically acceptable range.

Within the therapeutic compound, the anionic group(s) is covalently attached to a carrier molecule. Suitable carrier molecules include carbohydrates, polymers, peptides, peptide derivatives, aliphatic groups, alicyclic groups, heterocyclic groups, aromatic groups or combinations thereof. A carrier molecule can be substituted, e.g. with one or more amino, nitro, halogen, thiol or hydroxy groups.

As used herein, the term "carbohydrate" is intended to include substituted and unsubstituted mono-, oligo-, and polysaccharides. Monosaccharides are simple sugars usually of the formula $C_6H_{12}O_6$ that can be combined to form oligosaccharides or polysaccharides. Monosaccharides include enantiomers and both the D and L stereoisomers of monosaccharides. Carbohydrates can have multiple anionic groups attached to each monosaccharide moiety. For example, in sucrose octasulfate, four sulfate groups are attached to each of the two monosaccharide moieties.

As used herein, the term "polymer" is intended to include molecules formed by the chemical union of two or more combining subunits called monomers. Monomers are molecules or compounds which usually contain carbon and are of relatively low molecular weight and simple structure. A monomer can be converted to a polymer by combination with itself or other similar molecules or compounds. A polymer may be composed of a single identical repeating subunit or multiple different repeating subunits (copolymers). Polymers within the scope of this invention include substituted and unsubstituted vinyl, acryl, styrene and carbohydrate-derived polymers and copolymers and salts thereof. In one embodiment, the polymer has a molecular weight of approximately 800–1000 Daltons. Examples of polymers with suitable covalently attached anionic groups (e.g., sulfonates or sulfates) include poly(2-acrylamido-2-methyl-1 -propanesulfonic acid); poly(2-acrylamido-2-methyl-1-propanesulfonic acid-co-acrylonitrile); poly(2-acrylamido-2-methyl-1-propanesulfonic acid-co-styrene); poly(vinylsulfonic acid); poly(sodium 4-styrenesulfonic acid); and sulfates and sulfonates derived from: poly(acrylic acid); poly(methyl acrylate); poly(methyl methacrylate); and poly(vinyl alcohol); and pharmaceutically acceptable salts thereof. Examples of carbohydrate-derived polymers with suitable covalently attached anionic groups include those of the formula:

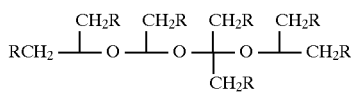

wherein R is $SO_3-$ or $OSO_3-$; and pharmaceutically acceptable salts thereof.

Peptides and peptide derivatives can also act as carrier molecules. The term "peptide" includes two or more amino acids covalently attached through a peptide bond. Amino acids which can be used in peptide carrier molecules include those naturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. The term amino acid further includes analogs, derivatives and congeners of naturally occurring amino acids, one or more of which can be present in a peptide derivative. For example, amino acid analogs can have lengthened or shortened side chains or variant side chains with appropriate functional groups. Also included are the D and L stereoisomers of an amino acid when the structure of the amino acid admits of stereoisomeric forms. The term "peptide derivative" further includes compounds which contain molecules which mimic a peptide backbone but are not amino acids (so-called peptidomimetics), such as benzodiazepine molecules (see e.g. James, G. L. et al. (1993) *Science* 260:1937–1942). The anionic groups can be attached to a peptide or peptide derivative through a functional group on the side chain of certain amino acids or other suitable functional group. For example, a sulfate or sulfonate group can be attached through the hydroxy side chain of a serine residue. A peptide can be designed to interact with a binding site for a basement membrane constituent (e.g., HSPG) in an amyloidogenic protein (as described above). Accordingly, in one embodiment, the peptide comprises four amino acids and anionic groups (e.g., sulfonates) are attached to the first, second and fourth amino acid. For example, the peptide can be Ser-Ser-Y⁻Ser, wherein an anionic group is attached to the side chain of each serine residue and Y is any amino acid. In addition to peptides and peptide derivatives, single amino acids can be used as carriers in the therapeutic compounds of the invention. For example, cysteic acid, the sulfonate derivative of cysteine, can be used.

The term "aliphatic group" is intended to include organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "amino" means $-NH_2$; the term "nitro" means $-NO_2$; the term "halogen" designates $-F$, $-Cl$, $-Br$ or $-I$; the term "thiol" means SH; and the term "hydroxyl" means $-OH$. Thus, the term "alkylamino" as used herein means an alkyl group, as defined above, having an amino group attached thereto. The term "alkylthio" refers to an alkyl group, as defined above, having a sulfhydryl group attached thereto. The term "alkylcarboxyl" as used herein means an alkyl group, as defined above, having a carboxyl group attached thereto. The term "alkoxy" as used herein means an alkyl group, as defined above, having an oxygen atom, attached thereto. Representative alkoxy groups include methoxy, ethoxy, propoxy, tert-butoxy and the like. The terms "alkenyl" and "alkynyl" refer to unsaturated aliphatic groups analogous to alkyls, but which contain at least one double or triple bond respectively.

The term "alicyclic group" is intended to include closed ring structures of three or more carbon atoms. Alicyclic groups include cycloparaffins or naphthenes which are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, $-CF_3$, $-CN$, or the like.

The term "heterocyclic group" is intended to include closed ring structures in which one or more of the atoms in the ring is an element other than carbon, for example, nitrogen, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, $-CF_3$, $-CN$, or the like.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The therapeutic compound of the invention can be administered in a pharmaceutically acceptable vehicle. As used herein "pharmaceutically acceptable vehicle" includes any and all solvents, dispersion media, coatings, antibacterial and antifingal agents, isotonic and absorption delaying agents, and the like which are compatible with the activity of the compound and are physiologically acceptable to the subject. An example of a pharmaceutically acceptable vehicle is buffered normal saline (0.15 molar NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

In a preferred embodiment of the method of the invention, the therapeutic compound administered to the subject is comprised of at least one sulfonate group covalently attached to a carrier molecule, or a pharmaceutically acceptable salt thereof. Accordingly, the therapeutic compound can have the formula:

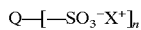

wherein Q is a carrier molecule; $X^+$ is a cationic group; and n is an integer. Suitable carrier molecules and cationic groups are those described hereinbefore. The number of sulfonate groups ("n") is selected such that the biodistribution of the compound for an intended target site is not prevented while maintaining activity of the compound as discussed earlier. In one embodiment, n is an integer between 1 and 10. In another embodiment, n is an integer between 3 and 8. As described earlier, therapeutic compounds with multiple sulfonate groups can have the sulfonate groups spaced such that the compound interacts optimally with an HSPG binding site within an amyloidogenic protein.

In preferred embodiments, the carrier molecule for a sulfonate(s) is a lower aliphatic group (e.g., a lower alkyl, lower alkenyl or lower alkynyl), a heterocyclic group, a disaccharide, a polymer or a peptide or peptide derivative. Furthermore, the carrier can be substituted, e.g. with one or more amino, nitro, halogen, thiol or hydroxy groups. In certain embodiments, the carrier molecule for a sulfonate(s) is an aromatic group.

Examples of suitable sulfonated polymeric therapeutic compounds include poly(2-acrylamido-2-methyl-1-propanesulfonic acid); poly(2-acrylamido-2-methyl-1-propanesulfonic acid-co-acrylonitrile); poly(2-acrylamido-2-methyl-1-propanesulfonic acid-co-styrene); poly (vinylsulfonic acid); poly(sodium 4-styrenesulfonic acid); a sulfonic acid derivative of poly(acrylic acid); a sulfonic acid derivative of poly(methyl acrylate); a sulfonic acid derivative of poly(methyl methacrylate); and a sulfonate derivative of poly(vinyl alcohol); and pharmaceutically acceptable salts thereof.

A preferred sulfonated polymer is poly(vinylsulfonic acid) (PVS) or a pharmaceutically acceptable salt thereof, preferably the sodium salt thereof. In one embodiment, PVS having a molecular weight of about 800–1000 Daltons is used. PVS may be used as a mixture of stereoisomers or as a single active isomer.

A preferred sulfonated disaccharide is a fully or partially sulfonated sucrose, or pharmaceutically acceptable salt thereof, such as sucrose octasulfonate. Other sulfonated saccharides include 5-deoxy-1,2-O-isopropylidene-α-D-xylofuranose-5-sulfonic acid (XXIII, shown as the sodium salt).

Preferred lower aliphatic sulfonated compounds for use in the invention include ethanesulfonic acid; 2-aminoethanesulfonic acid (taurine); cysteic acid (3-sulfoalanine or α-amino-β-sulfopropionic acid); 1-propanesulfonic acid; 1,2-ethanedisulfonic acid; 1,3-propanedisulfonic acid; 1,4-butanedisulfonic acid; 1,5-pentanedisulfonic acid; and 4-hydroxybutane-1-sulfonic acid (VIII, shown as the sodium salt); and pharmaceutically acceptable salts thereof. Other aliphatic sulfonated compounds contemplated for use in the invention include 1-butanesulfonic acid (XLVII, shown as the sodium salt), 2-propanesulfonic acid (XLIX, shown as the sodium salt), 3-pentanesulfonic acid (L, shown as the sodium salt), 4-heptanesulfonic acid (LII, shown as the sodium salt), 1-decanesulfonic acid (XLVIII, shown as the sodium salt); and pharmaceutically acceptable salts thereof. Sulfonated substituted aliphatic compounds contemplated for use in the invention include 3-amino-1-propanesulfonic acid (XXII, shown as the sodium salt), 3-hydroxypropanesulfonic acid sulfate (XXXV, shown as the disodium salt), 1,7-dihydroxy-4-heptanesulfonic acid (LIII, shown as the sodium salt); and pharmaceutically acceptable salts thereof. Yet other sulfonated compounds contemplated for use in the invention include 2-[(4-pyridinyl)amido]ethanesulfonic acid (LIV, depicted as the sodium salt), and pharmaceutically acceptable salts thereof.

Preferred heterocyclic sulfonated compounds include 3-(N-morpholino)propanesulfonic acid; and tetrahydrothiophene-1,1-dioxide-3,4-disulfonic acid; and pharmaceutically acceptable salts thereof.

Aromatic sulfonated compounds include 1,3-benzenedisulfonic acid (XXXVI, shown as the disodium salt), 2,5-dimethoxy-1,4-benzenedisulfonic acid (depicted as the disodium salt, XXXVII, or the dipotassium salt, XXXIX), 4-amino-3-hydroxy-1-naphthalenesulfonic acid (XLIII), 3,4-diamino-1-naphthalenesulfonic acid (XLIV); and pharmaceutically acceptable salts thereof.

In another embodiment of the method of the invention, the therapeutic compound administered to the subject is comprised of at least one sulfate group covalently attached to a carrier molecule, or a pharmaceutically acceptable salt thereof. Accordingly, the therapeutic compound can have the formula:

wherein Q is a carrier molecule; $X^+$ is a cationic group; and n is an integer. Suitable carrier molecules and cationic groups are those described hereinbefore. The number of sulfate groups ("n") is selected such that the biodistribution of the compound for an intended target site is not prevented while maintaining activity of the compound as discussed earlier. In one embodiment, n is an integer between 1 and 10. In another embodiment, n is an integer between 3 and 8. As described earlier, therapeutic compounds with multiple sulfate groups can have the sulfate groups spaced such that the compound interacts optimally with an HSPG binding site within an amyloidogenic protein.

In preferred embodiments, the carrier molecule for a sulfate(s) is a lower aliphatic group (e.g., a lower alkyl, lower alkenyl or lower alkynyl), an aromatic group, a disaccharide, a polymer or a peptide or peptide derivative. Furthermore, the carrier can be substituted, e.g. with one or more amino, nitro, halogen, thiol or hydroxy groups.

Examples of suitable sulfated polymeric therapeutic compounds include poly(2-acrylamido-2-methyl-propyl sulfuric acid); poly(2-acrylamido-2-methyl-propyl sulfuric acid-co-acrylonitrile); poly(2-acrylamido-2-methyl-propyl sulfuric acid-co-styrene); poly(vinylsulfuric acid); poly(sodium 4-styrenesulfate); a sulfate derivative of poly(acrylic acid); a sulfate derivative of poly(methyl acrylate); a sulfate derivative of poly(methyl methacrylate); and a sulfate derivative of poly(vinyl alcohol); and pharmaceutically acceptable salts thereof.

A preferred sulfated polymer is poly(vinylsulfuric acid) or pharmaceutically acceptable salt thereof.

A preferred sulfated disaccharide is sucrose octasulfate or pharmaceutically acceptable salt thereof. Other sulfated saccharides contemplated for use in the invention include the acid form of methyl-α-D-glucopyranoside 2,3-disulfate (XVI), methyl 4,6-O-benzylidene-α-D-glucopyranoside 2,3-disulfate (XVII), 2,3,4,3',4'-sucrose pentasulfate (XXXIII), 1,3:4,6-di-O-benzylidene-D-mannitol 2,5-disulfate (XLI), D-mannitol 2,5-disulfate (XLII), 2,5-di-O-benzyl-D-mannitol tetrasulfate (XLV); and pharmaceutically acceptable salts thereof.

Preferred lower aliphatic sulfated compounds for use in the invention include ethyl sulfuric acid; 2-aminoethan-1-ol sulfuric acid; 1-propanol sulfuric acid; 1,2-ethanediol disulfuric acid; 1,3-propanediol disulfuric acid; 1,4-butanediol disulfuric acid; 1,5-pentanediol disulfuric acid; and 1,4-butanediol monosulfuric acid; and pharmaceutically acceptable salts thereof. Other sulfated aliphatic compounds contemplated for use in the invention include the acid form of 1,3-cyclohexanediol disulfate (XL), 1,3,5-heptanetriol trisulfate (XIX), 2-hydroxymethyl-1,3-propanediol trisulfate (XX), 2-hydroxymethyl-2-methyl-1,3-propanediol trisulfate (XXI), 1,3,5,7-heptanetetraol tetrasulfate (XLVI), 1,3,5,7,9-nonane pentasulfate (LI); and pharmaceutically acceptable salts thereof. Other sulfated compounds contemplated for use in the invention include the acid form of 2-amino-2-hydroxymethyl-1,3-propanediol trisulfate (XXIV), 2-benzyloxy-1,3-propanediol disulfate (XXIX), 3-hydroxypropylsulfamic acid sulfate (XXX)2,2'-iminoethanol disulfate (XXXI), N,N-bis(2-hydroxyethyl) sulfamic acid disulfate (XXXII); and pharmaceutically acceptable salts thereof.

Preferred heterocyclic sulfated compounds include 3-(N-morpholino)propanesulfuric acid; and tetrahydrothiophene-1,1-dioxide-3,4-diol disulfuric acid; and pharmaceutically acceptable salts thereof.

A further aspect of the invention includes pharmaceutical compositions for treating amyloidosis. The therapeutic compounds in the methods of the invention, as described hereinbefore, can be incorporated into a pharmaceutical composition in an amount effective to inhibit amyloidosis in a pharmaceutically acceptable vehicle.

In one embodiment, the pharmaceutical compositions of the invention include a therapeutic compound that has at least one sulfonate group covalently attached to a carrier molecule, or a pharmaceutically acceptable salt thereof, in an amount sufficient to inhibit amyloid deposition, and a pharmaceutically acceptable vehicle. The therapeutic composition can have the formula:

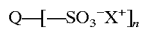

wherein Q is a carrier molecule; $X^+$ is a cationic group; and n is an integer selected such that the biodistribution of the compound for an intended target site is not prevented while maintaining activity of the compound.

In another embodiment, the pharmaceutical compositions of the invention include a therapeutic compound that has at least one sulfate group covalently attached to a carrier molecule, or a pharmaceutically acceptable salt thereof, in an amount sufficient to inhibit amyloid deposition, and a pharmaceutically acceptable vehicle. The therapeutic compound can have the following formula:

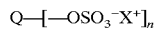

wherein Q is a carrier molecule; $X^+$ is a cationic group; and n is an integer selected such that the biodistribution of the compound for an intended target site is not prevented while maintaining activity of the compound.

The invention further contemplates the use of prodrugs which are converted in vivo to the therapeutic compounds of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the therapeutic compound. For example, an anionic group, e.g., a sulfate or sulfonate, can be esterified, e.g, with a methyl group or a phenyl group, to yield a sulfate or sulfonate ester. When the sulfate or sulfonate ester is administered to a subject, the ester is cleaved, enzymatically or non-enzymatically, reductively or hydrolytically, to reveal the anionic group. Such an ester can be cyclic, e.g., a cyclic sulfate or sultone, or two or more anionic moieties may be esterified through a linking group. Exemplary cyclic compounds include, for example, 2-sulfobenzoic acid (LV), propane sultone (LVI), butane sultone (LVII), 1,3-butanediol cyclic sulfate (LVIII), α-chloro-α-hydroxy-o-toluenesulfonic acid sultone (LIX), and 6-nitronaphth-[1,8-cd]-1,2,-oxathiole 2,2-dioxide (LX). In a preferred embodiment, the prodrug is a cyclic sulfate or sultone. An anionic group can be esterified with moieties (e.g., acyloxymethyl esters) which are cleaved to reveal an intermediate compound which subsequently decomposes to yield the active compound. In another embodiment, the prodrug is a reduced form of a sulfate or sulfonate, e.g., a thiol, which is oxidized in vivo to the therapeutic compound. Furthermore, an anionic moiety can be esterified to a group which is actively transported in vivo, or which is selectively taken up by target organs. The ester can be selected to allow specific targeting of the therapeutic moieties to particular organs, as described below for carrier moieties.

Carrier molecules useful in the therapeutic compounds include carrier molecules previously described, e.g. carbohydrates, polymers, peptides, peptide derivatives, aliphatic groups, alicyclic groups, heterocyclic groups, aromatic groups or combinations thereof. Suitable polymers include substituted and unsubstituted vinyl, acryl, styrene and carbohydrate-derived polymers and copolymers and salts thereof. Preferred carrier molecules include a lower alkyl group, a heterocyclic group, a disaccharide, a polymer or a peptide or peptide derivative.

Carrier molecules useful in the present invention may also include moieties which allow the therapeutic compound to be selectively delivered to a target organ or organs. For example, if delivery of a therapeutic compound to the brain is desired, the carrier molecule may include a moiety capable of targeting the therapeutic compound to the brain, by either active or passive transport (a "targeting moiety"). Illustratively, the carrier molecule may include a redox moiety, as described in, for example, U.S. Pat. Nos. 4,540,564 and 5,389,623, both to Bodor. These patents disclose drugs linked to dihydropyridine moieties which can enter the brain, where they are oxidized to a charged pyridinium species which is trapped in the brain. Thus, drug accumulates in the brain. Exemplary pyridine/dihdropyridine compounds of the invention include sodium 1-(3-sulfopropyl)-1,4-dihydropyridine (LXI), sodium 2-(nicotinylamido)-ethanesulfonate (LXII), and 1-(3-sulfopropyl)-pyridinium betaine (LXIII). Other carrier moieties include compounds, such as amino acids or thyroxine, which can be passively or actively transported in vivo. An illustrative compound is phenylalanyltaurine (LXIX), in which a taurine molecule is conjugated to a phenylalanine (a large neutral amino acid). Such a carrier moiety can be metabolically removed in vivo, or can remain intact as part of an active compound. Structural mimics of amino acids (and other actively transported moieties) are also useful in the invention (e.g., 1-(aminomethyl)-1-(sulfomethyl)-cyclohexane (LXX)). Other exemplary amino acid mimetics include p-(sulfomethyl)phenylalanine (LXXII), p-(1,3-disulfoprop-2-yl)phenylalanine (LXXIII), and O-(1,3-disulfoprop-2-yl) tyrosine (LXXIV). Exemplary thyroxine mimetics include compounds LXXV, LXVI, and LXXVII. Many targeting moieties are known, and include, for example, asialoglycoproteins (see, e.g. Wu, U.S. Pat. No. 5,166,320) and other ligands which are transported into cells via receptor-mediated endocytosis (see below for further examples of targeting moieties which may be covalently or non-covalently bound to a carrier molecule). Furthermore, the therapeutic compounds of the invention may bind to amyloidogenic proteins in the circulation and thus be transported to the site of action.

The targeting and prodrug strategies described above can be combined to produce a compound that can be transported as a prodrug to a desired site of action and then unmasked to reveal an active compound. For example, the dihydropyrine strategy of Bodor (see supra) can be combined with a cyclic prodrug, as for example in the compound 2-(1-methyl-1,4-dihydronicotinyl)amidomethyl-propanesultone (LXXI).

In one embodiment, the therapeutic compound in the pharmaceutical compositions is a sulfonated polymer, for example poly(2-acrylamido-2-methyl-1-propanesulfonic acid); poly(2-acrylamido-2-methyl-1-propanesulfonic acid-co-acrylonitrile); poly(2-acrylamido-2-methyl-1-propanesulfonic acid-co-styrene); poly(vinylsulfonic acid); poly(sodium 4-styrenesulfonic acid); a sulfonate derivative of poly(acrylic acid); a sulfonate derivative of poly(methyl acrylate); a sulfonate derivative of poly(methyl methacrylate); and a sulfonate derivative of poly(vinyl alcohol); and pharmaceutically acceptable salts thereof.

In another embodiment, the therapeutic compound in the pharmaceutical compositions is a sulfated polymer, for example poly(2-acrylamido-2-methyl-1-propanesulfuric acid); poly(2-acrylamido-2-methyl-1-propanesulfuric acid-co-acrylonitrile); poly(2-acrylamido-2-methyl-1-propanesulfuric acid-co-styrene); poly(vinylsulfuric acid); poly(sodium 4-styrenesulfate); a sulfate derivative of poly (acrylic acid); a sulfate derivative of poly(methyl acrylate); a sulfate derivative of poly(methyl methacrylate); and a sulfate derivative of poly(vinyl alcohol); and pharmaceutically acceptable salts thereof.

Preferred therapeutic compounds for inclusion in a pharmaceutical composition for treating amyloidosis of the invention include poly(vinylsulfuric acid); poly (vinylsulfonic acid); sucrose octasulfate; a partially or fully sulfonated sucrose; ethyl sulfuric acid; ethanesulfonic acid; 2-aminoethanesulfonic acid (taurine); 2-(aminoethyl) sulfuric acid; cysteic acid (3-sulfoalanine or α-amino-β-sulfopropionic acid); 1-propanesulfonic acid; propyl sulfuric acid; 1,2-ethanedisulfonic acid; 1,2-ethanedioldisulfuric acid; 1,3-propanedisulfonic acid; 1,3-propanediol disulfuric acid; 1,4-butanedisulfonic acid; 1,4-butanediol disulfuric acid; 1,5-pentanedisulfonic acid; 1,5-pentanediol disulfuric acid; 4-hydroxybutane-1-sulfonic acid; tetrahydrothiophene-1,1-dioxide-3,4-disulfonic acid; 3-(N-morpholino)propanesulfonic acid; and pharmaceutically acceptable salts thereof.

In the methods of the invention, amyloid deposition in a subject is inhibited by administering a therapeutic compound of the invention to the subject. The term subject is intended to include living organisms in which amyloidosis can occur. Examples of subjects include humans, monkeys, cows, sheep, goats, dogs, cats, mice, rats, and transgenic species thereof. Administration of the compositions of the present invention to a subject to be treated can be carried out using known procedures, at dosages and for periods of time effective to inhibit amyloid deposition in the subject. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to inhibit amyloid deposition in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention (e.g., poly (vinylsulfonate sodium salt)) is between 5 and 500 mg/kg of body weight/per day. In an aqueous composition, preferred concentrations for the active compound (i.e., the therapeutic compound that can inhibit amyloid deposition) are between 5 and 500 mM, more preferably between 10 and 100 mM, and still more preferably between 20 and 50 mM. For taurine, particularly preferred aqueous concentrations are between 10 and 20 mM.

As demonstrated in the Exemplification, the therapeutic compounds of the invention are effective when administered orally. Accordingly, a preferred route of administration is oral administration. Alternatively, the active compound may be administered by other suitable routes such subcutaneous, intravenous, intraperitoneal, etc. administration (e.g. by injection). Depending on the route of administration, the active compound may be coated in a material to protect the compound from the action of acids and other natural conditions which may inactivate the compound.

The compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); gp120 (Schreier et al. (1994) *J. Biol. Chem.* 269:9090); see also K. Keinanen; M. L. Laukkanen (1994) *FEBS Lett.* 346:123; J.

J. Killion; I. J. Fidler (1994) *Immunomethods* 4:273. In a preferred embodiment, the therapeutic compounds of the invention are formulated in liposomes; in a more preferred embodiment, the liposomes include a targeting moiety.

Delivery and in vivo distribution can also be affected by alteration of an anionic group of compounds of the invention. For example, anionic groups such as carboxylate or tetrazole can be employed instead of, or in addition to, sulfate or sulfonate moieties, to provide compounds with desirable pharmocokinetic, pharmacodynamic, biodistributive, or other properties. Exemplary tetrazole-substituted compounds include 3-(1H-tetrazol-5-yl)-9H-thioxanthen-9-one 10,10-dioxide (LXIV), 5,5-dithiobis(1-phenyltetrazole) (LXV), 1H-tetrazole (LXVI), 5-phenyl-1H-tetrazole (LXVII), and 5-(2-aminoethanoic acid)-1H-tetrazole (LXVIII), and the like; and their pharmaceutically aceptable salts. Exemplary carboxylate-substituted compounds include dicarboxylic acids such as adipic acid, azelaic acid, 3,3-dimethylglutaric acid, suberic acid, succinic acid, and the like, and their pharmaceutically acceptable salts.

To administer the therapeutic compound by other than parenteral administration, it may be necessary to coat the compound with, or co-administer the compound with, a material to prevent its inactivation. For example, the therapeutic compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of amyloid deposition in subjects.

Active compounds are administered at a therapeutically effective dosage sufficient to inhibit amyloid deposition in a subject. A "therapeutically effective dosage" preferably inhibits amyloid deposition by at least about 20%, more preferably by at least about 40%, even more preferably by at least about 60%, and still more preferably by at least about 80% relative to untreated subjects. The ability of a compound to inhibit amyloid deposition can be evaluated in an animal model system that may be predictive of efficacy in inhibiting amyloid deposition in human diseases, such as the model system used in the Examples. Alternatively, the ability of a compound to inhibit amyloid deposition can be evaluated by examining the ability of the compound to inhibit an interaction between an amyloidogenic protein and a basement membrane constituent, e.g., using a binding assay such as that described hereinbefore.

The method of the invention is useful for treating amyloidosis associated with any disease in which amyloid deposition occurs. Clinically, amyloidosis can be primary, secondary, familial or isolated. Amyloids have been categorized by the type of amyloidogenic protein contained within the amyloid. Non-limiting examples of amyloids which can be inhibited, as identified by their amyloidogenic protein, are as follows (with the associated disease in parentheses after the amyloidogenic protein): β-amyloid (Alzheimer's disease, Down's syndrome, hereditary cerebral hemorrhage amyloidosis [Dutch]); amyloid A (reactive [secondary] amyloidosis, familial Mediterranean Fever, familial amyloid nephropathy with urticaria and deafness [Muckle-Wells syndrome]); amyloid κL-chain or amyloid λL-chain (idiopathic [primary], myeloma or macroglobulinemia-associated); Aβ2M (chronic hemodialysis); ATTR (familial amyloid polyneuropathy [Portuguese, Japanese, Swedish], familial amyloid cardiomyopathy [Danish], isolated cardiac amyloid, systemic senile amyloidosis); AIAPP or amylin (adult onset diabetes, insulinoma); atrial naturetic factor (isolated atrial amyloid); procalcitonin (medullary carcinoma of the thyroid); gelsolin (familial amyloidosis [Finnish]); cystatin C (hereditary cerebral hemorrhage with amyloidosis [Icelandic]); AApoA-I (familial amyloidotic polyneuropathy [Iowa]); AApoA-II (accelerated senescence in mice); fibrinogen-associated amyloid; lysozyme-associated amyloid; and AScr or PrP-27 (Scrapie, Creutzfeldt-Jacob disease, Gerstmann-Straussler-Scheinker syndrome, bovine spongiforn encephalitis).

The sulfated and sulfonated compounds used in the methods described herein are commercially available (e.g. Sigma Chemical Co., St. Louis, Mo., or Aldrich Chemical Co., Milwaukee, Wis.) and/or can be synthesized by standard techniques known in the art (see, e.g., Stone, G. C. H. (1936) *J. Am. Chem. Soc.,* 58:488). In general, sulfated compounds were synthesized from the corresponding alcohols. The alcohols corresponding to XIX and XX were obtained by reduction of 1,3-acetonedicarboxylic acid and triethyl methanetricarboxylate, respectively, which are commercially available. Representative syntheses of active compounds used herein are described in further detail in Example 10.

In certain embodiments of the invention, Congo red is excluded from sulfonated compounds used in the method of the invention.

In certain embodiments of the invention, the following sulfated compounds are excluded from use in the method of the invention: dextran sulfate 500, τ-carrageenan, λ-carrageenan, dextran sulfate 8, κ-carrageenan, pentosan polysulfate, and/or heparan.

In certain embodiments of the invention, the compositions and methods of the invention are used to inhibit amyloid deposition in amyloidosis wherein the amyloidogenic protein is not the protease-resistant form of a prion protein, AScr (also known as PrP-27).

The invention is further illustrated by the following examples which should not be construed as further limiting the subject invention. The contents of all references, issued patents, and published patent applications cited throughout this application are hereby incorporated by reference. A demonstration of efficacy of the therapeutic compounds of the present invention in the mouse model described in the examples is predictive of efficacy in humans.

EXEMPLIFICATION

In the following examples, a well-characterized mouse model of amyloidosis was used. In this in vivo system, animals receive an inflammatory stimulus and amyloid enhancing factor. For acute amyloidosis (i.e., short term amyloid deposition), the inflammatory stimulus is $AgNO_3$. For chronic amyloidosis (ongoing amyloid deposition), the inflammatory stimulus is lipopolysaccharide (LPS). Amyloid deposition (AA amyloid) in the spleens of mice was measured with and without therapeutic treatment.

Example 1

The following methodologies were used:

Animals

All mice were of the CD strain (Charles Rivers, Montreal, Quebec) and weighing 25–30 g.

Animal Treatment All animals received $AgNO_3$ (0.5 ml, 2% solution) subcutaneously in the back, and amyloid enhancing factor (AEF) 100 μg intravenously. The preparation of amyloid enhancing factor has been described previously in Axelrad, M. A. et al. ("Further Characterization of Amyloid Enhancing Factor" *Lab. Invest.* 47:139–146 (1982)). The animals were divided into several groups one of which was an untreated control group which was sacrificed six days later. The remaining animals were divided into those which received poly (vinylsulfonate sodium salt) (PVS) at 50 mg, 40 mg, 20 mg, or 10 mg by intraperitoneal injection every 12 hours or sucrose octasulfate ammonium salt (SOA) at 73 mg or 36.5 mg every 8 hours by IP injection. The PVS used in this and all subsequent Examples was a mixture of stereoisomers. Surviving animals were sacrificed on the 5th day of treatment. In all cases the PVS or SOA was dissolved in a sterile aqueous carrier.

Tissue Preparation

At the termination of the experiments, the animals were sacrificed by cervical dislocation and the spleens, livers, and kidneys were fixed in 96% ethanol, 1% glacial acetic acid and 3% water as described in Lyon, A. W. et al. ("Co-deposition of Basement Membrane Components During the Induction of Murine Splenic AA Amyloid" *Lab. Invest.* 64:785–790 (1991)). Following fixation, the tissues were embedded in paraffin, 8–10 micron sections were cut and stained with Congo Red without counterstain as described in Puchtler, H. et al. ("Application of Thiazole Dyes to Amyloid Under Conditions of Direct Cotton Dyeing: Correlation of Histochemical and Chemical Data" *Histochemistry* 77:431–445 (1983)). The histologic sections viewed under polarized light were assessed by image analysis for the percent of spleen occupied by amyloid. In the case of the experiments with sucrose octasulfate, the tissues were immunostained with an antibody to the SAA protein (described in Lyon A. W. et al. *Lab Invest.* 64:785–790 (1991)) and the immunostained sections assessed by image analysis for the percent of tissue section occupied by amyloid.

Viability of Animals

All control animals survived the experiment without incident. In the case of the animals undergoing therapy, all animals given sucrose octasulfate at 73 mg/injection succumbed prior to the termination of the experiment. Animals receiving 36.5 mg of sucrose octasulfate/injection all survived. Of those animals receiving PVS (molecular weight 900–1000) in each dosage group, approximately half to one-third of the animals succumbed prior to the termination of the experiment. In all cases of animal deaths prior to the end of the experiments, the cause of death was uncontrolled intraperitoneal hemorrhage.

Effects of Agents on Amyloid Deposition

The effect of sucrose octasulfate at 36.5 mg/injection is shown below in Table 1. The mean area of spleen occupied by amyloid in control animals was 7.8%±1.5% S.E.M. In animals receiving the therapeutic agent the mean area was 3.2%±0.5% S.E.M. The difference is significant at a $p \leq 0.02$.

TABLE 1

Effect of Sucrose Octasulfate Ammonium Salt
on AA Amyloid Deposition In vivo in Mouse Spleen
% Area Occupied by Amyloid

| Untreated | 7.8 + 1.5 | n = 5 |
|---|---|---|
| Sucrose OctaSO$_4$ | 3.2 + 0.5 | n = 5 |
| | p ≦ 0.02 | |

In the case of PVS, the data are shown in FIG. 1. There was a profound inhibition of amyloid deposition at all doses with the suggestion of a dose-dependent effect. An effective dose range is between 5 and 500 mg/kg of body weight/per day.

Preliminary assessment of the plasma level of the precursor of inflammation-associated amyloidosis, SAA, has shown that there is no difference between the animals being treated with PVS and those untreated.

The method of administering the agents of the present invention is believed to have had an effect upon the mortality rate of the animals. Intraperitoneal injection was selected as providing a large membrane surface for ease of access to the circulating system. However, like heparan, the compounds of the present invention exhibit anti-coagulant properties. Repeated injections through the peritoneal wall induced severe hemorrhaging and ultimately resulted in filling the peritoneal cavity, with loss of blood causing death. While subcutaneous injection would result in slower absorption of the active compound, it is less likely that this route would cause hemorrhaging to such an extent as to cause death. Oral administration of the compounds was performed in subsequent experiments (see below).

Example 2

Figure 4:
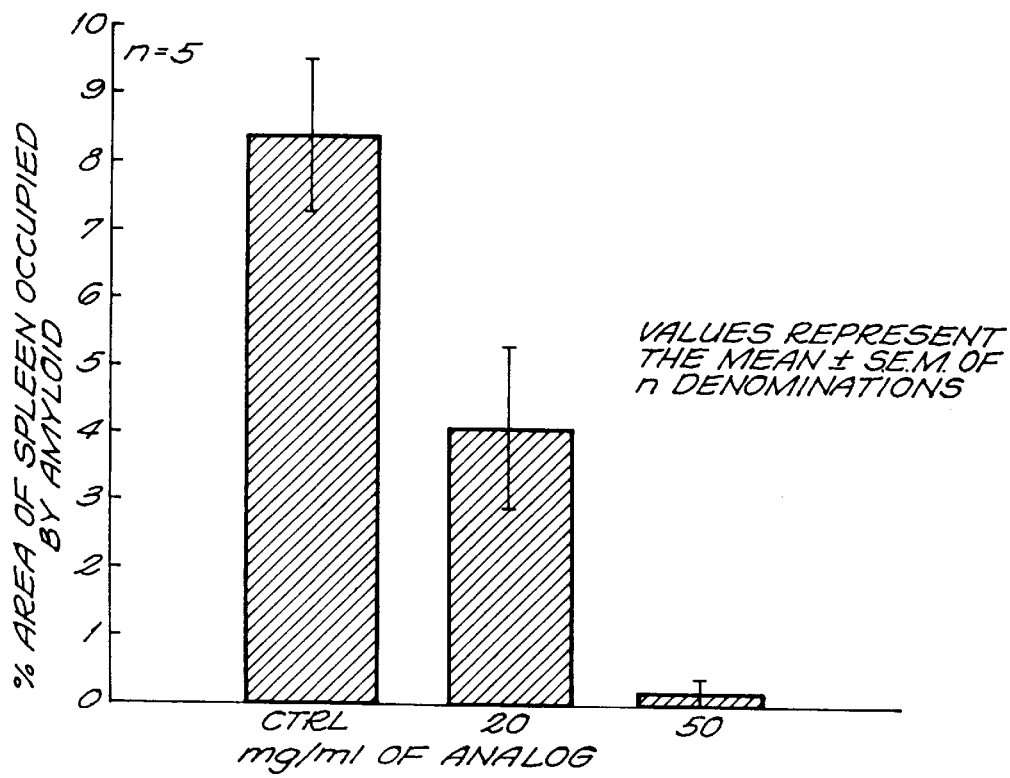
FIG. 4 is a bar graph illustrating the effect of poly(vinylsulfonate sodium salt) administered orally on in vivo AA amyloid deposition in mouse spleen.

Swiss white mice weighing 25–30 g were given Amyloid Enhancing Factor (AEF) and AgNO$_3$ as described previously (Kisilevsky, R. and Boudreau, L. (1983) "The kinetics of amyloid deposition: I. The effect of amyloid enhancing factor and splenectomy" Lab. Invest., 48, 53–59), to induce amyloidosis. Twenty four (24) hours later they were divided into three groups. One group served as a control and was maintained on standard laboratory mouse chow and tap water ad lib. A second group received the standard chow but its water contained 20 mg/ml of poly(vinylsulfonate sodium salt) (PVS). The third group had 50 mg/ml of PVS in its drinking water. Fluid intake in both groups was the same. All animals were sacrificed on day six (6) of the experiment, their spleens collected, prepared for sectioning, spleen sections stained with Congo red (Puchtler, H., et al. (1983) "Application of Thiazole Dyes to Amyloid under Conditions of Direct Cotton Dyeing: Correlation of Histochemical and Chemical Data" Histochemistry, 77, 431–445), and the percent area occupied by amyloid assessed by an image analysis apparatus and program (MCID M2, Imaging Research Inc., Brock University, St. Catherines, Ontario, Canada). As shown in FIG. 4, oral administration of PVS interferes with amyloid deposition in a dose dependent manner.

Example 3

Figure 5:
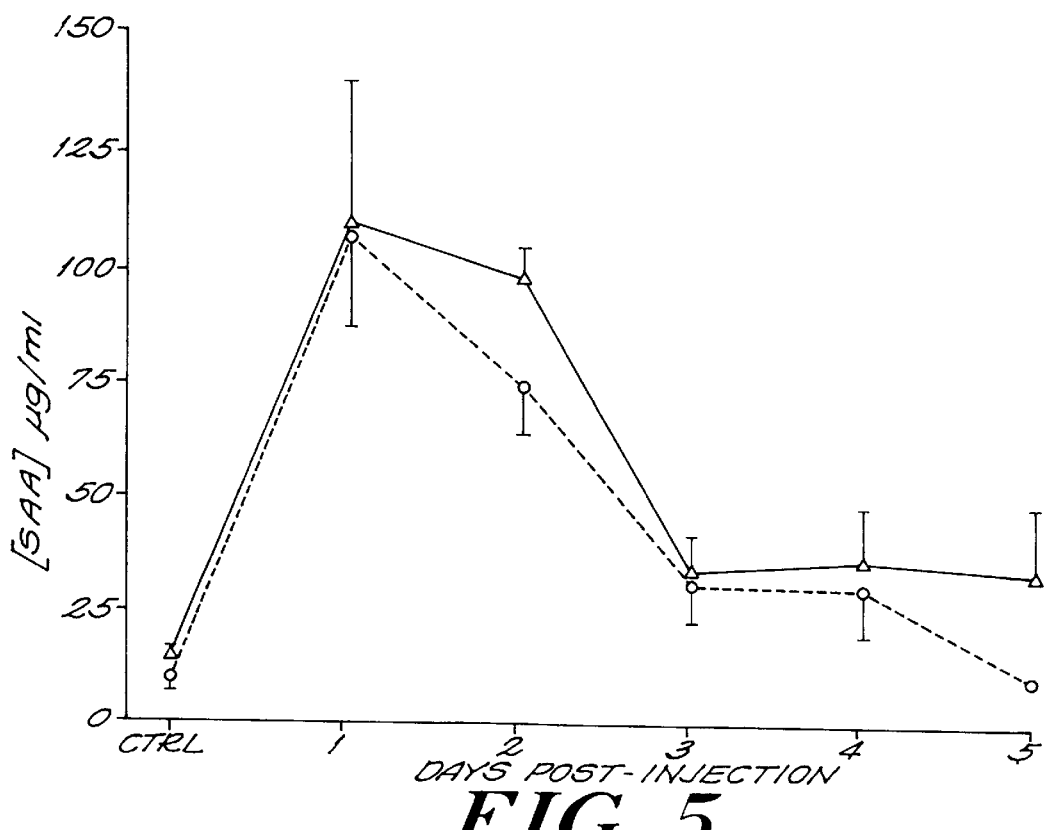
FIG. 5 is a graph illustrating the blood level of the amyloid precursor, SAA, over time for animals receiving poly(vinylsulfonate sodium salt) (open circles) and control animals (triangles).

Since it was possible that PVS was inhibiting the hepatic synthesis of the amyloid precursor, and thus failure to deposit amyloid was due to the absence of the precursor pool, the effect of PVS on the blood level of the amyloid precursor (SAA) during the course of the experiment was determined. Animals received AEF+AgNO$_3$ as described above and were divided into two groups. Group 1 received no further treatment. Twenty four hours later, Group 2 received 50 mg of PVS by intraperitoneal injection every 12 hours for a period of 5 days. To plot the level of SAA during this process, each animal (controls and experimentals) was bled from the tail (≈25 μl) each day. The SAA levels in these samples were determined by a solid phase ELISA procedure (described in Brissette, L., et al. (1989) J. Biol. Chem., 264, 19327–19332). The results are shown in FIG. 5. The open circles represent the data from the PVS-treated mice, while the triangles show the data from the non-treated animals. SAA levels were equivalent in treated and untreated animals, demonstrating that PVS does not mediate its effect by preventing the synthesis of SAA.

Example 4

Figure 6:
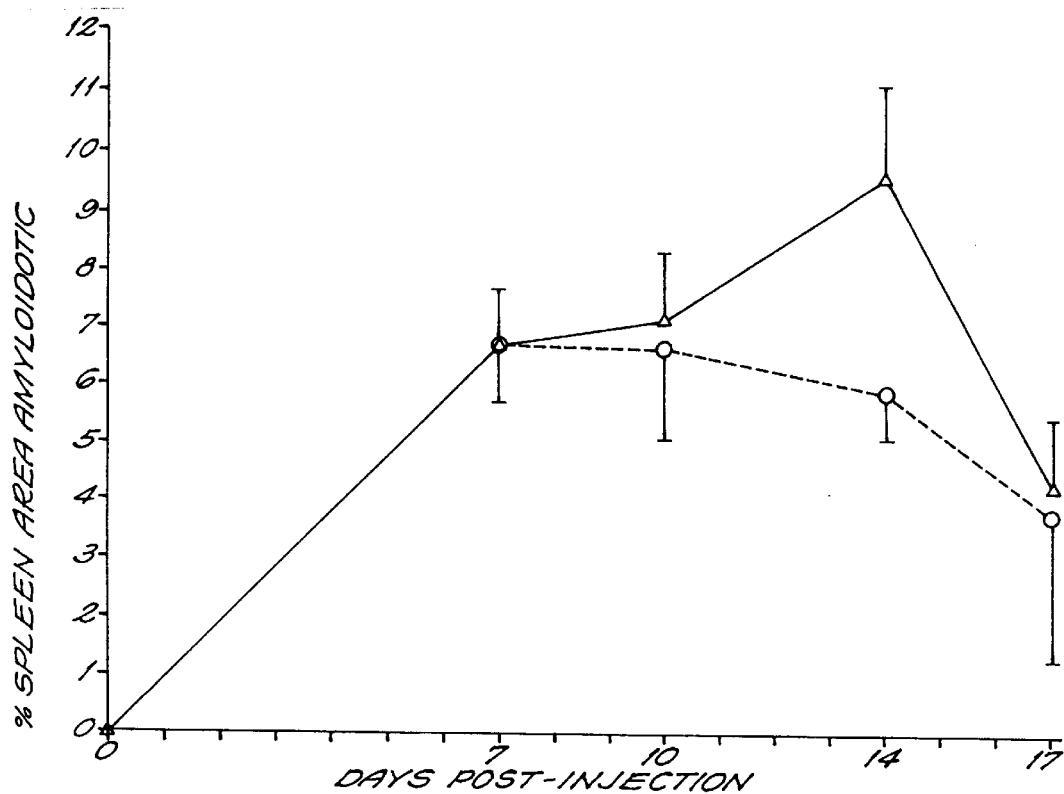
FIG. 6 is a graph illustrating the effect of orally administered poly(vinylsulfonate sodium salt) on the course of AA amyloid deposition in mouse spleen when amyloid deposits were already present prior to treatment of the animals. The triangles represent the control animals and the open circles represent the treated animals.

In the above described experiments, therapy with PVS was begun 24 hours into the amyloid induction protocol. This does not mimic a clinical situation where the patient usually has well established amyloid. To approximate a more realistic clinical situation, a separate set of experiments were performed in which PVS treatment was begun after amyloid deposition had already begun. Animals received AEF+AgNO$_3$, as described above, remained on tap water for 7 days, after which they were separated into two groups. Group 1 remained on standard food and tap water. Group 2 remained on standard food but had 50 mg/ml of PVS added to their drinking water. To assess the effect of PVS on the course of amyloid deposition after amyloid was already present, five animals in each group were sacrificed on days 7, 10, 14, and 17. The spleens were processed and evaluated as described above. The data are shown in FIG. 6. Control animals (triangles) continued to deposit amyloid for 14 days, following which the quantity of amyloid began to decrease. This latter decrease is most likely due to the fact that only one injection of AgNO$_3$, the inflammatory stimulus, was given and, after 14 days, the SAA levels are known to decrease (Kisilevsky, R., Boudreau, L. and Foster, D. (1983) "Kinetics of amyloid deposition. II. The effects of dimethylsulfoxide and colchicine therapy" Lab. Invest., 48, 60–67). In the absence of precursor, further amyloid cannot be deposited and existing deposits are mobilized (Kisilevsky, R. and Boudreau, L. (1983) "The kinetics of amyloid deposition: I. The effect of amyloid enhancing factor and splenectomy" Lab. Invest., 48, 53–59). In contrast, the treated group of animals (open circles) stopped deposition of amyloid within 3 days of being placed on PVS. This demonstrates that PVS is effective at inhibiting ongoing deposition of amyloid.

Example 5

Figure 7:
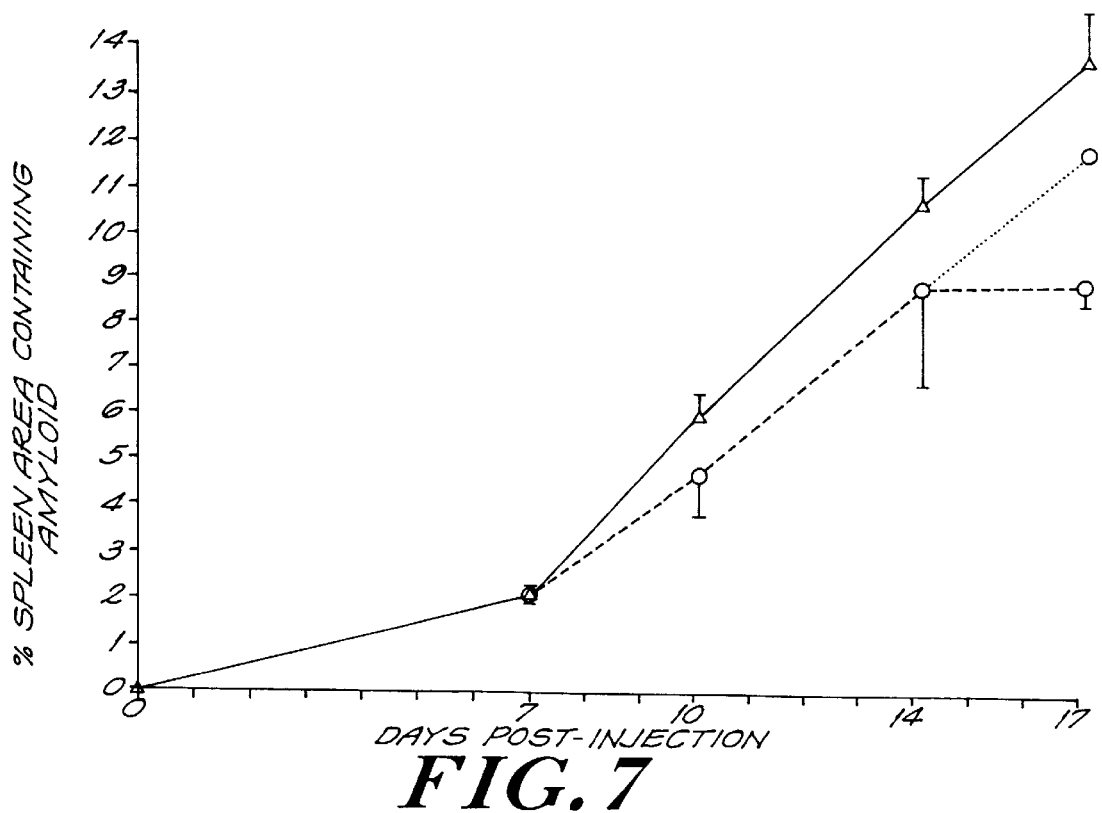
FIG. 7 is a graph illustrating the effect of orally administered poly(vinylsulfonate sodium salt) on splenic amyloid deposition when the inflammatory stimulus is maintained during the course of the experiment. The triangles represent the control animals and the open circles represent the treated animals.

To maintain the inflammation and the blood SAA levels, and allow amyloid to be continuously deposited for the duration of a longer term experiment, the nature of the inflammatory stimulus was changed. So as to maintain the inflammation, animals received lipopolysaccharide (LPS, 20 μg)+AEF on day 0 and LPS was given by intraperitoneal injection every 2nd day. On day seven (7), the animals were separated into two groups as described in Example 4. Assessment of amyloid over the course of the experiment proceeded as described in Example 4. The data are shown in FIG. 7. The control group (triangles) continued to deposit amyloid for the entire 17 day period. Those receiving PVS apparently stopped depositing amyloid by day 14 (open circles and dashed line). The data on day 17 represent 4 animals per group as one animal was omitted from this time period. The quantity of amyloid in this particular individual was so far removed from all other data points (treated or not, it was 21%) that it is believed that this was a statistically valid procedure. If this individual is included, the curve is represented by the dotted line and the remaining open circle. It should be pointed out that animals receiving PVS began to develop a significant diarrhea as the experiment proceeded.

Example 6

Figure 8:
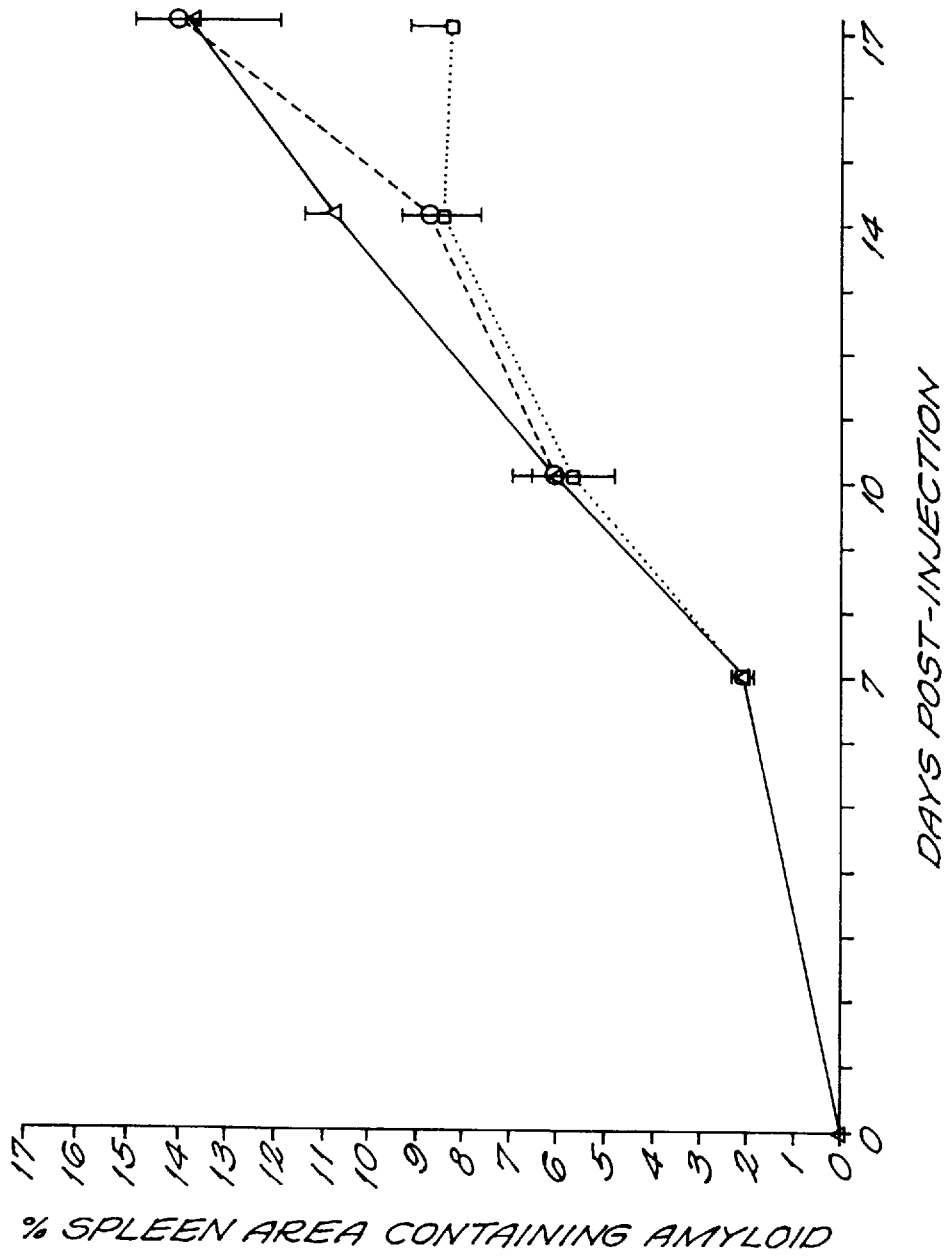
FIG. 8 is a graph illustrating the effect of orally administered ethane monosulfonate, sodium salt (EMS) on in vivo AA splenic amyloid deposition. The triangles represent the control animals, the open circles represent animals receiving 2.5 mg/ml of EMS in their drinking water, and the open squares represent animals receiving 6 mg/ml of EMS in their drinking water.

In this experiment, another sulfonated compound, ethane monosulfonic acid was used to inhibit amyloidosis. Ethane monosulfonic acid, sodium salt, (EMS) is structurally the monomeric unit of PVS. Animals were given LPS+AEF as in Experiment 5, but on day seven EMS was used in the drinking water as the therapeutic agent. On day seven, the animals were divided into three groups. Group 1 was the untreated group. Group 2 received 2.5 mg/ml EMS in their drinking water. Group 3 received 6 mg/ml in their drinking water. Animals were sacrificed on days 7, 10, 14, and 17. These animals did not develop gastro-intestinal problems. These data are shown in FIG. 8. Animals receiving 6 mg/ml EMS in their drinking water (open squares) stopped depositing amyloid after day 14. Those receiving 2.5 mg/ml EMS (open circles) seemed to have an abortive therapeutic effect, with a slight diminution in the rate of amyloid deposition at day 14 which was not maintained by day 17.

Example 7

The Influence of PVS on HSPG Binding to the Alzheimer's Amyloid Precursor Protein (Beta APP)

Figure 2:
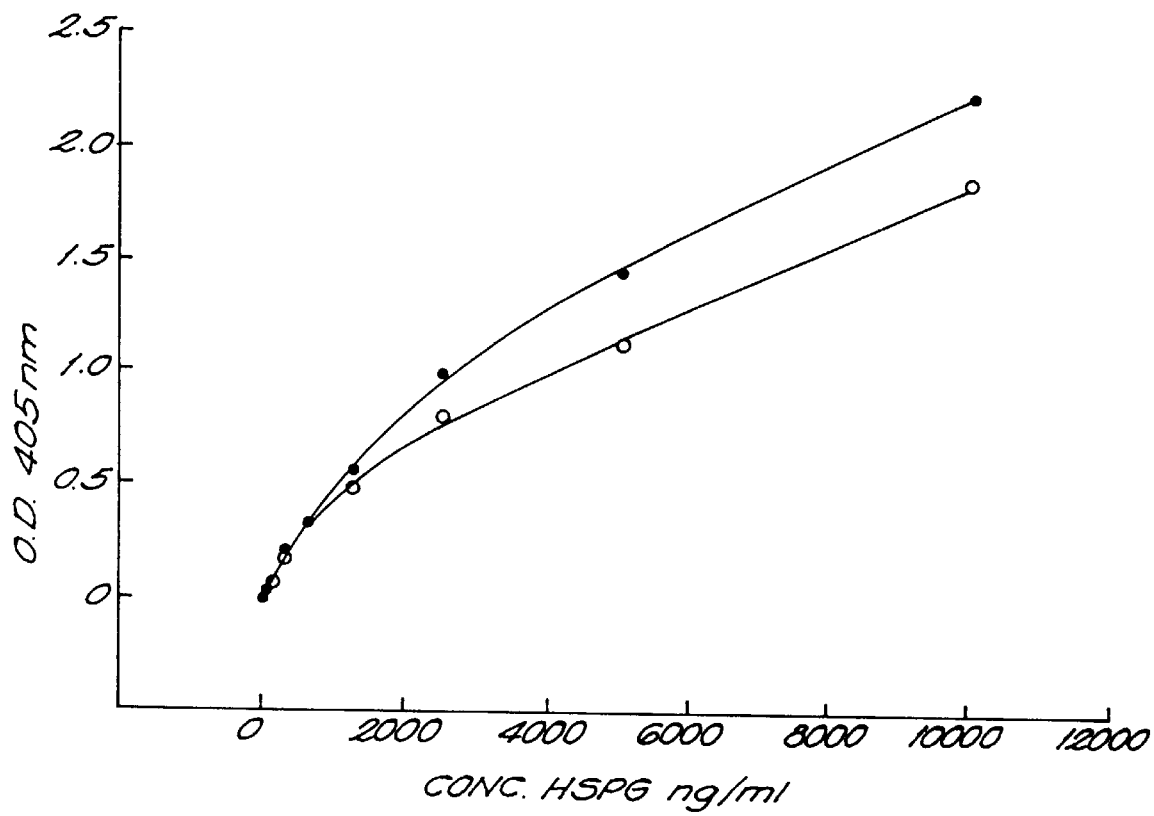
FIG. 2 is a graph illustrating the effect of poly(vinylsulfonate sodium salt) on heparan sulfate proteoglycan binding to P-APP in tris-buffered saline (TBS).
Figure 3:
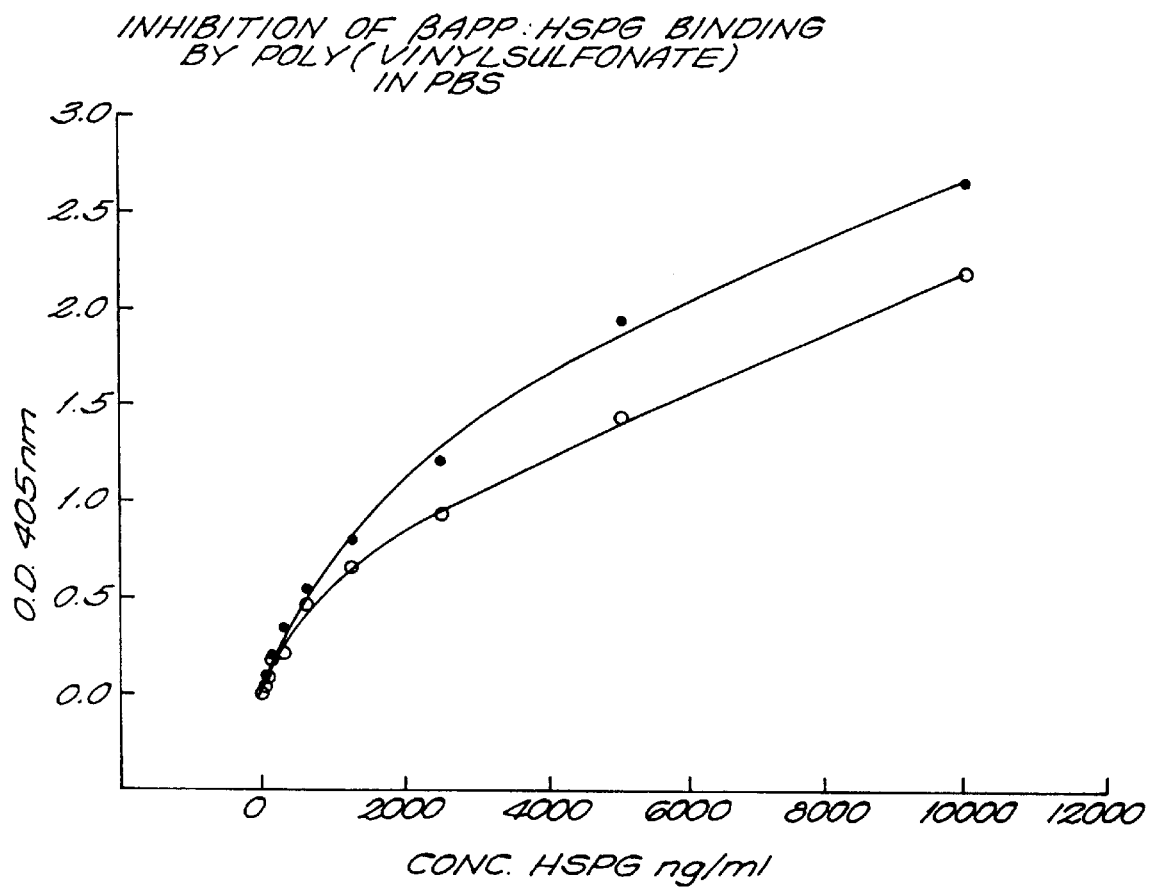
FIG. 3 is a graph illustrating the effect of poly(vinylsulfonate sodium salt) on heparan sulfate proteoglycan binding to P-APP in phosphate buffered saline (PBS).

The binding of heparan sulfate proteoglycan to beta APP was assessed using an enzyme-linked immunosorbent assay technique as described in Narindrasorasak, S. et al. ("High Affinity Interactions Between the Alzheimer's Beta-Amyloid Precursor Proteins and the Basement Membrane Form of Heparan Sulfate Proteoglycan" *J. Biol. Chem.* 266:12878–12883 (1991)). Polystyrene microtiter plates (Linbro, Flow Laboratories) were coated with a 100 μl solution, 1 μg/ml of β-APP, in 20 mM NaHCO₃ buffer, pH 9.6. After overnight incubation at 4° C., the plates were rinsed with 0.15M NaCl, 20 mM Tris-Cl, pH 7.5 (TBS). The plates were then incubated with 150 μl of 1% bovine serum albumin (BSA) in TBS for 2 hours at 37° C. to block the residual hydrophobic surface on the wells. After rinsing with TBS containing 0.05% (w/v) Tween 20 (TBS-Tween), 100 μl of various concentrations of HSPG in TBS-Tween were added alone or 500 μg/ml of PVS, either in Tris-buffered saline (TBS) or phosphate-buffered saline (PBS), was included in the binding assay to assess the effect of PVS on HSPG binding to β-APP. The plates were left overnight at 4° C. to permit maximum binding of HSPG to β-APP. The plates were then washed extensively and incubated 2 hours at 37° C. with 100 μl of anti-HSPG diluted in TBS-Tween containing 0.1% BSA. The plates were washed again and incubated for another 2 hours with 100 μl of goat anti-rabbit IgG conjugated with alkaline phosphatase (1:2000 dilution) in TBS-Tween containing BSA as above. Finally, after further washing, the bound antibodies were detected by adding an alkaline phosphatase substrate solution (100 μl) containing 2 mg/ml p-nitrophenyl phosphate, 0.1 mM ZnCl₂, 1 mM MgCl₂, and 100 mM glycine, pH 10. The plates were left at room temperature for 15–120 minutes. The enzyme reaction was stopped by addition of 50 μl of 2M NaOH. The absorbence of the released p-nitrophenol was measured at 405 mn with a Titertek Multiscan/MCC 340 (Flow Laboratories). The amounts of HSPG bound were determined by the net $A_{405}$ after subtracting the A from blank wells in which the HSPG incubation step was omitted. The effect of PVS on HSPG: beta-APP binding is illustrated in FIG. 2 (in TBS) and FIG. 3 (in PBS). Approximately 30–50% inhibition of binding is demonstrated with this compound.

Example 8

Acute amyloidosis was elicited in mice with $AgNO_3$ and amyloid enhancing factor as described in Examples 1 and 2. Twenty-four hours later, the animals were divided into a control group and six test groups. The control group was maintained on standard laboratory mouse chow and tap water ad lib. The test groups received standard chow but their water contained 50 mM of one of the following six compounds: sodium ethanesulfonate, sodium 2-aminoethanesulfonate (taurine), sodium 1-propanesulfonate, sodium 1,2-ethanedisulfonate, sodium 1,3-propanedisulfonate, or sodium 1,4-butanedisulfonate. Water intake was approximately equivalent for all groups. After six days, the animals were sacrificed and their spleens were processed as described in Example 2. For preliminary analysis, the spleen sections were examined visually under a microscope for differences in amyloid deposition in the treated animals versus the control animals.

The results indicated that animals treated with sodium 1-propanesulfonate, sodium 1,2-ethanedisulfonate, or sodium 1,3-propanedisulfonate had less amyloid deposition than control animals. Under the conditions used in this experiment, animals treated with sodium ethanesulfonate, taurine sodium salt, or sodium 1,4-butanedisulfonate were not observed to have less amyloid deposition than control animals. However, these compounds may exhibit effectiveness under other conditions, for example sodium ethanesulfonate has been observed to inhibit chronic amyloid deposition (see Example 6) and taurine inhibits acute amyloid deposition at other concentrations (see Example 9).

This experiment suggests that oral administration of sulfonated lower aliphatics such as sodium 1-propanesulfonate, sodium 1,2-ethanedisulfonate and sodium 1,3-propanedisulfonate can inhibit amyloid deposition in an acute amyloidogenic system.

Example 9

Figure 9:
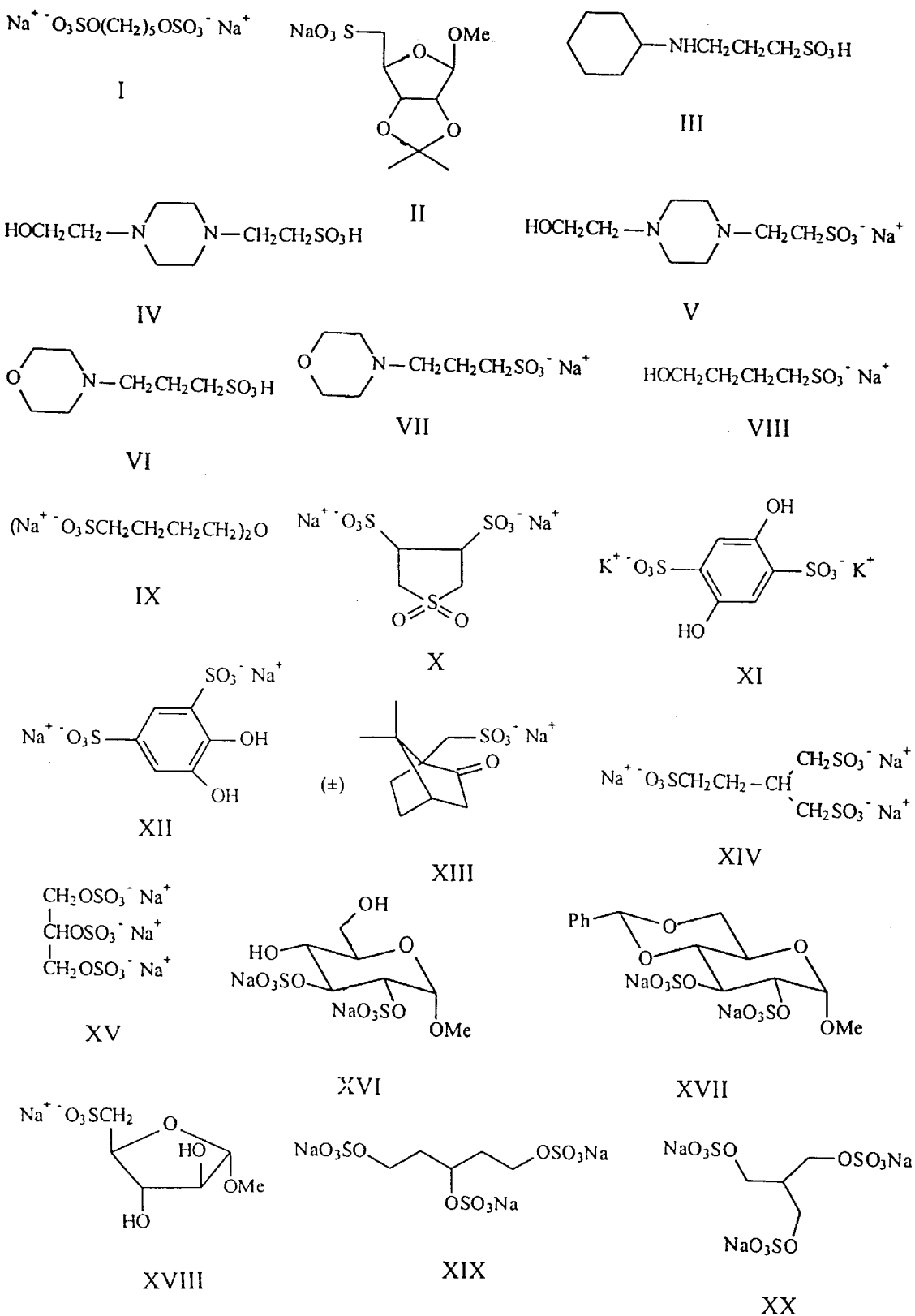
FIGS. 9–14 depict the chemical structures of compounds described in the specification.
Figure 10:
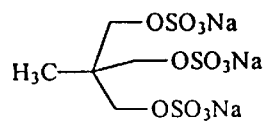
Figure 10:
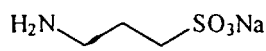
Figure 10:
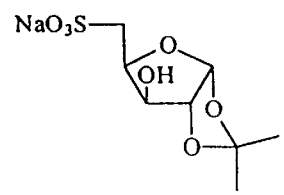
Figure 10:
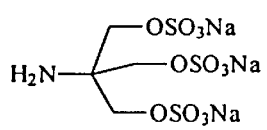
Figure 10:
Figure 10:
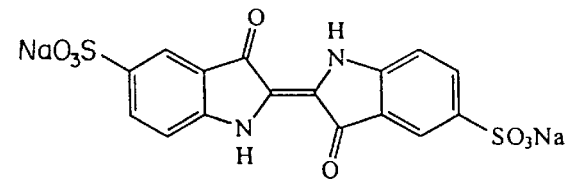
Figure 10:
Figure 10:
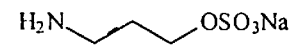
Figure 10:
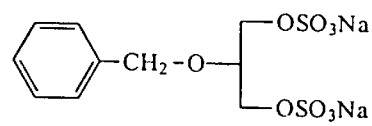
Figure 10:
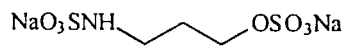
Figure 10:
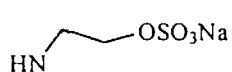
Figure 10:
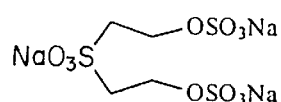
Figure 10:
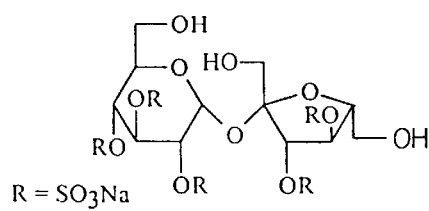
Figure 10:
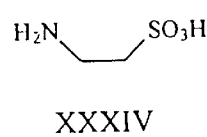
Figure 10:
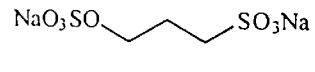
Figure 10:
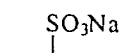
Figure 10:
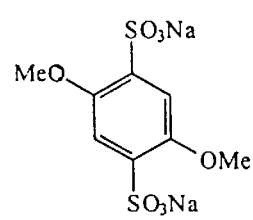
Figure 10:
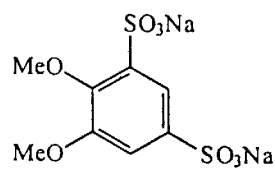
Figure 10:
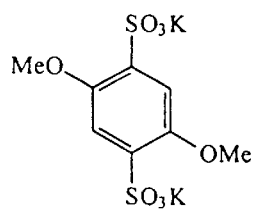
Figure 10:
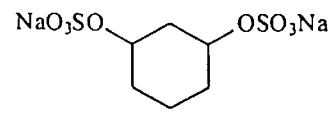
Figure 11:
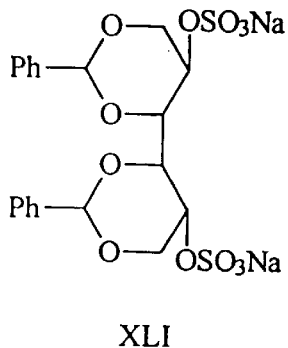
Figure 11:
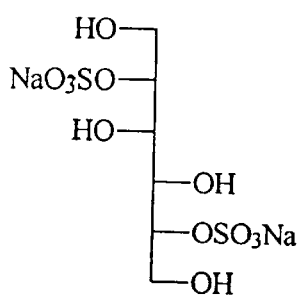
Figure 11:
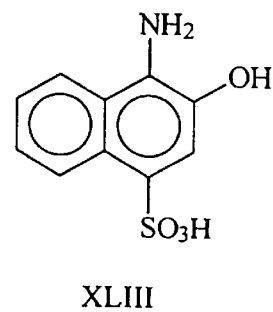
Figure 11:
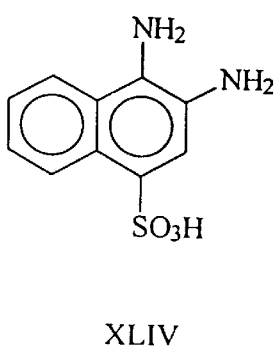
Figure 11:
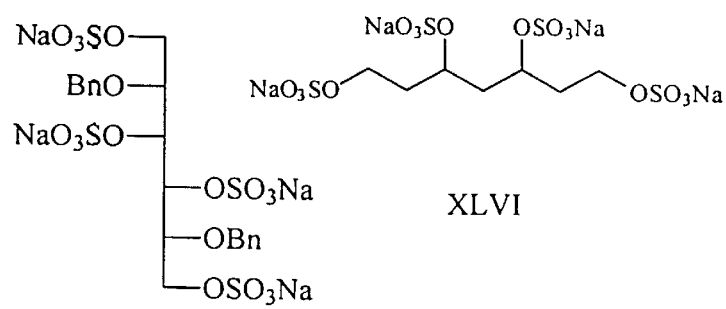
Figure 11:
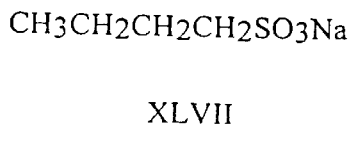
Figure 11:
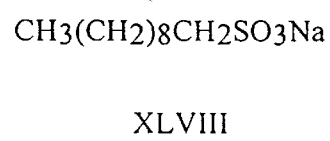
Figure 11:
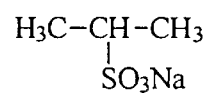
Figure 11:
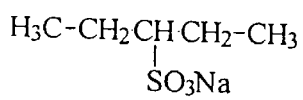
Figure 11:
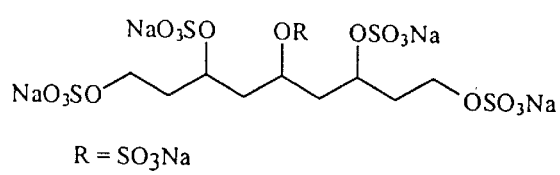
Figure 11:
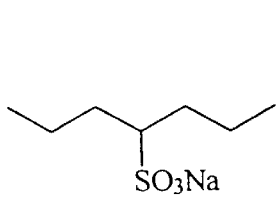
Figure 11:
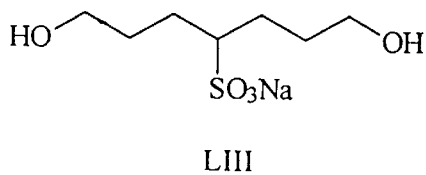
Figure 11:
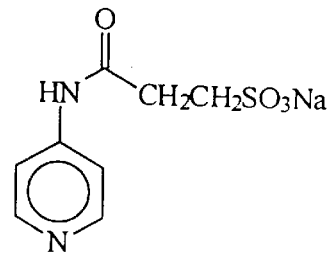
Figure 12:
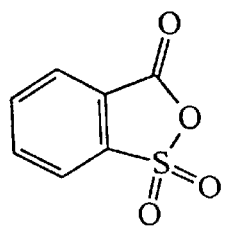
Figure 12:
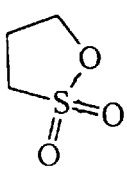
Figure 12:
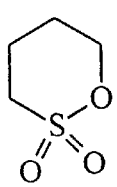
Figure 12:
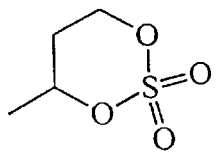
Figure 12:
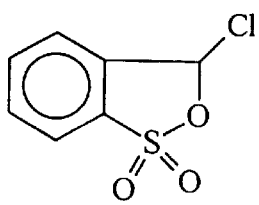
Figure 12:
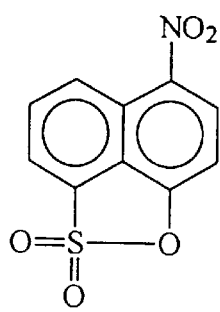
Figure 12:
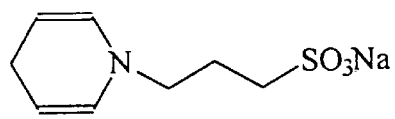
Figure 12:
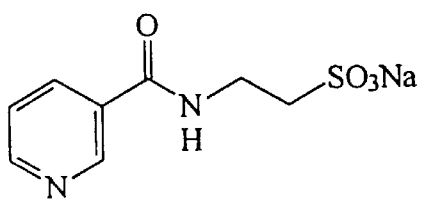
Figure 12:
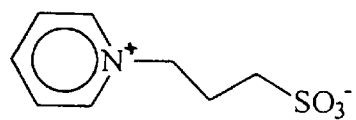
Figure 13:
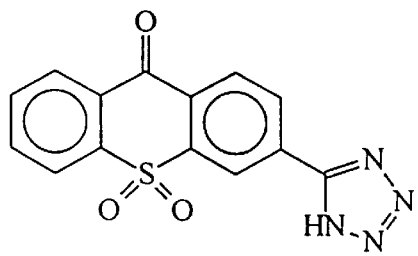
Figure 13:
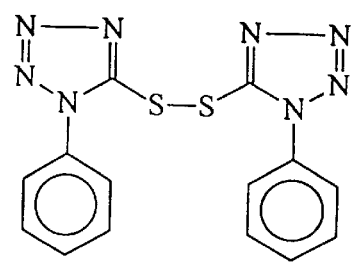
Figure 13:
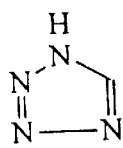
Figure 13:
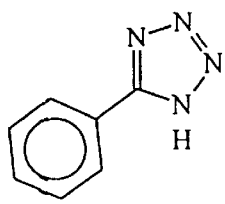
Figure 13:
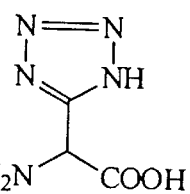
Figure 13:
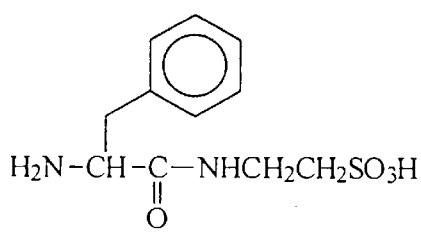
Figure 13:
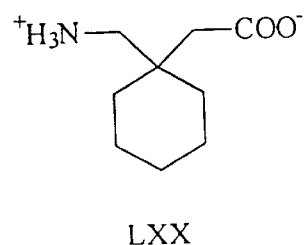
Figure 13:
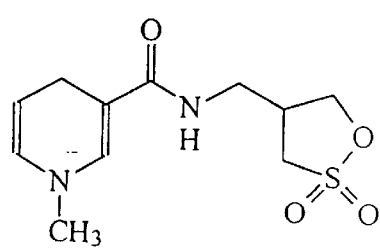
Figure 13:
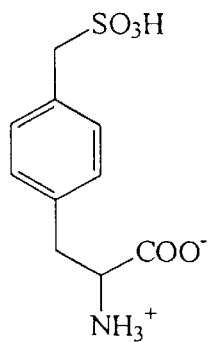
Figure 13:
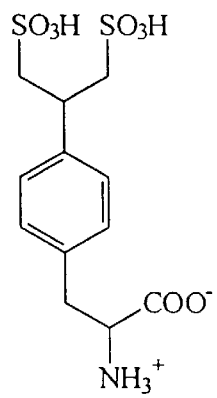
Figure 13:
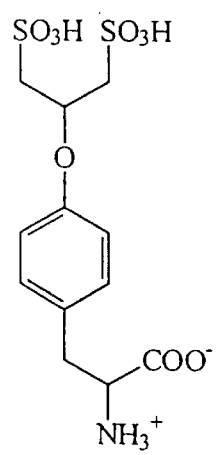
Figure 14:
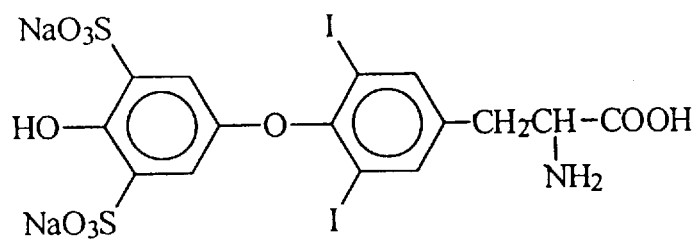
Figure 14:
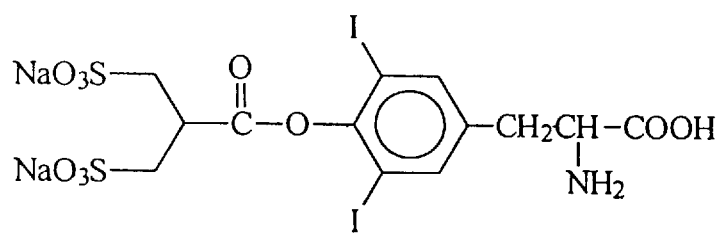
Figure 14:
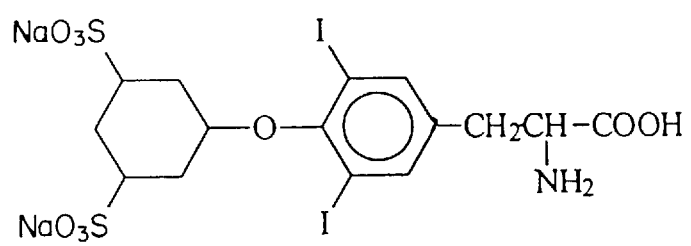

In view of the preliminary results described in Example 8, further experiments were conducted to determine the effect of a panel of sulfated or sulfonated compounds on acute amyloid deposition. Acute amyloidosis was induced in mice as described in Examples 1 and 2. Twenty-four hours later, the animals were divided into a control group and test groups. The control group was maintained on standard laboratory mouse chow and tap water ad lib. The test groups received standard chow but their water contained 20 or 50 mM of one of the compounds listed in Table 2, below (the chemical structures of the WAS compounds listed in Table 2 are depicted in FIGS. 9 and 10). One compound, taurine, was tested at concentrations of 5 mM, 10 mM, 20 mM, and 50 mM. All compounds were dissolved in water containing 1.0% sucrose. Water intake was approximately equivalent for all groups. After six days, the animals were sacrificed and their spleens were processed as described in Example 2.

The results are summarized in Table 2, below.

TABLE 2

Effect of Sulfated and Sulfonated Compounds
on AA Amyloid Depositions In vivo Mouse Spleen

| Compound | Concentration (mM) | Amyloid Deposition* | Standard Error |
|---|---|---|---|
| 1,5-Pentanedisulfonate† | 50 | 76 | 11 |
|  | 20 | 60 | 20 |
| 1,6-Hexanedisulfonate† | 50 | 117 | 17 |
|  | 20 | 98 | 26 |
| 1,2-Ethanediol disulfate† | 50 | 8 | 2 |
|  | 20 | 36 | 10 |
| 1,3-Propanediol disulfate† | 50 | 11 | 4 |
|  | 20 | 32 | 11 |
| 1,4-Butanediol disulfate† | 50 | 54 | 22 |
|  | 20 | 44 | 11 |
| Taurine (XXXIV) | 50 | 68 | 15 |
|  | 20 | 45 | 23 |
|  | 10 | 34 | 16 |
|  | 5 | 95 | 33 |
| 1,5-Pentanediol disulfate, sodium salt (I) | 50 | 79 | 22 |
|  | 20 | 80 | 23 |
| Methyl 5-deoxy-2,3-O-isopropylidene-β-D-ribofuranoside-5-sulfonic acid, sodium salt (II) | 50 | 114 |  |
|  | 20 | 114 |  |
| 3-Cyclohexylamino-1-propane-sulfonic acid (III) | 50 | 55 |  |
|  | 20 | 74 |  |
| 4-(2-Hydroxyethyl)-1-piperazineethanesulfonic acid (IV) | 50 | 81 |  |
|  | 20 | 63 |  |
| 4-(2-Hydroxyethyl)-1-piperazineethanesulfonic acid, sodium salt (V) | 50 | 135 | 27 |
|  | 20 | 83 | 28 |
| 4-Morpholine-propanesulfonic acid (VI) | 50 | 56 | 13 |
|  | 20 | 102 | 24 |
| 4-Morpholine-propanesulfonic acid, sodium salt (VII) | 50 | 48 | 12 |
|  | 20 | 98 | 30 |
| 4-Hydroxybutanesulfonic acid, sodium salt (VIII) | 50 | 60 | 21 |
|  | 20 | 54 | 31 |
| Bis(4-sulfobutyl) ether disodium salt (IX) | 50 | 110 | 35 |
|  | 20 | 97 | 50 |
| Tetrahydro-3,4-thiophenedisulfonic acid-1,1-dioxide, disodium salt (X) | 50 | 61 | 13 |
|  | 20 | 117 | 28 |
| 2,5-Dihydroxy-1,4-benzenedisulfonic acid, dipotassium salt (XI) | 50 | 192 | 37 |
|  | 20 | 119 | 19 |
| 4,5-Dihydroxy-1,3-benzenedisulfonic acid, disodium salt (XII) | 50 | 158 | 19 |
|  | 20 | 130 | 28 |
| (±)-10-Camphorsulfonic acid, sodium salt (XIII) | 50 | 83 | 19 |
|  | 20 | 155 | 28 |
| 2-Sulfomethylbutane-1,4-disulfonic acid, trisodium salt (XIV) | 50 | 66 | 12 |
|  | 20 | 94 | 11 |
| Glycerol trisulfate, trisodium salt (XV) | 50 | 103 | 19 |
|  | 20 | 110 | 15 |
| Methyl 5-deoxy-α-D-arabinofuranoside-5-sulfonic acid, sodium salt (XVIII) | 50 | 100 | 18 |
|  | 20 | 86 | 30 |
| 1,3,5-Pentanetriol trisulfate, trisodium salt (XIX) | 50 | 56 |  |
|  | 20 | 53 |  |
| 2-Aminoethyl hydrogen sulfate (XXV) | 50 | 53 |  |
|  | 20 | 59 |  |
| Indigo Carmine (XXVI) | 50 | 51 |  |
| 2-Hydroxyethylsulfamic acid sulfate, disodium salt (XVII) | 50 | 71 |  |
| 3-Amino-1-propyl sulfate, sodium salt (XXVIII) | 50 | 100 |  |
|  | 20 | 102 |  |

TABLE 2-continued

Effect of Sulfated and Sulfonated Compounds
on AA Amyloid Depositions In vivo Mouse Spleen

| Compound | Concentration (mM) | Amyloid Deposition* | Standard Error |
|---|---|---|---|
| 2-Benzyloxy-1,3-propanediol disulfate, disodium salt (XXIX) | 50 | 81 |  |

†As the sodium salt.
*Amyloid deposition is given as a percentage of untreated control. All measurements are the average of 3–5 animals.

The results indicate that animals treated with sodium 1,2-ethanediol disulfate or sodium 1,3-propanediol disulfate had at least about a 65% decrease in amyloid deposition at 20 mM and at least about a 90% decrease in amyloid deposition at 50 mM. Animals treated with sodium 1,4-butanediol disulfate (50 mM), sodium 1,5-pentanedisulfonate (50 mM), taurine (sodium 2-aminoethanesulfonate) (10–20 mM), 3-(cyclohexylamino)-1-propane sulfonate (III) (50 mM), 4-(2-hydroxyethyl)-1-piperazine-ethanesulfonate (IV) (20 mM), 3-(N-morpholino)propanesulfonic acid (MOPS) (VI) or its sodium salt (VII) (50 mM), sodium tetrahydrothiophene-1, 1-dioxide-3,4-disulfate trihydrate (X), sodium 4-hydroxybutane-1-sulfonate (VIII) (50 mM), sodium 1,3, 5-pentanetriol trisulfate (XIX) (20 and 50 mM), 2-aminoethyl hydrogen sulfate (XXV) (20 and 50 mM), or indigo carmine (XXVI) (50 mM) had at least approximately a 40% decrease in amyloid deposition compared to untreated control animals. Taurine was effective at concentrations of 10–20 mM, as seen in this example, but less effective at 5 mM or 50 mM (see also Example 8).

Certain sulfated or sulfonated compounds were not effective in reducing the amount of amyloid deposition under the conditions employed, but may be effective in other embodiments. Earlier in vitro work demonstrated that dermatan sulfate and chondroitin 6-sulfate do not interfere with the binding of beta amyloid presursor protein to HSPG. Sodium (±)-10-camphorsulfonate (XIII), 4,5-dihydroxy-1,3-benzenedisulfonic acid, disodium salt (XII) and 2,5-dihydroxy-1,4-benzenedisulfonic acid, dipotassium salt (XI) were tested in the above-described mouse model and, as shown in Table 2, were found not to reduce amyloid deposition.

Example 10

In this example representative syntheses of two compounds used in the methods of the invention are described.

Sodium ethane-1,2-disulfonate

A mixture of 1,2-dibromoethane (37.6 g, 0.20 mol) and sodium sulfite (63.0 g, 0.5 mol) in water (225 mL) was heated at reflux temperature for 20 h. After the mixture was cooled in the refrigerator, crystals were collected. The crude product was repeatedly recrystallized from water-ethanol. The trace amount of inorganic salts was removed by treating the aqueous solution with a small amount of silver(I) oxide and barium hydroxide. The basic solution was neutralized with Amberlite-120 ion-exchange resin and treated three times with Amberlite-120 (sodium form) ion-exchange resin. After removal of the water, the product was recrystallized from water-ethanol to afford the title compound (30.5 g).

Sodium 1,3-propanedisulfonate

This compound was prepared by a modification of the method described in Stone, G. C. H. (1936) *J. Am. Chem.*

Soc., 58:488. 1,3-Dibromopropane (40.4 g, 0.20 mol) was treated with sodium sulfite (60.3 g, 0.50 mol) in water at reflux temperature for 48 h. Inorganic salts (sodium bromide and sodium sulfite) were removed by successive treatment of the resultant reaction mixture with barium hydroxide and silver(I)oxide. The solution was then neutralized with Amberlite-120 (acid form) and decolorized with Norit-A. Barium ions were removed by treatment of the aqueous solution with Amberlite-120 (sodium form) ion-exchange resin. The solvent was removed on a rotary evaporator, and the crude product was recrystallized from water-ethanol several times to give the title compound (42.5 g). The small amount of trapped ethanol was removed by dissolving the crystals in a minimum amount of water and then concentrating the solution to dryness. The pure product was further dried under high vacuum at 56° C. for 24 h: mp>300° C.; $^1$H NMR ($D_2O$) δ: 3.06–3.13 (m, 4H, H-1 and H-3), 2.13–2.29 (m, 2H, H-2); $^{13}$C NMR ($D_2O$) δ: 52.3 (C-1 and C-3), 23.8 (C-2).

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method for inhibiting amyloid deposition in a subject comprising administering to the subject an effective amount of a therapeutic compound, the therapeutic compound comprising at least one sulfonate group covalently attached to a carrier molecule, or a pharmaceutically acceptable salt thereof.

2. The method of claim 1, wherein the therapeutic compound is administered orally.

3. The method of claim 1, wherein the carrier molecule is selected from the group consisting of a polymer, a peptide, a peptidomimetic, an aliphatic group, an alicyclic group, a heterocyclic group, and combinations thereof.

4. The method of claim 3, wherein the carrier molecule is an aliphatic group.

5. The method of claim 4, wherein the therapeutic compound is selected from the group consisting of ethanesulfonic acid, 1,2-ethanedisulfonic acid, 1-propanesulfonic acid, 1,3-propanedisulfonic acid, 1,4-butanedisulfonic acid, 1,5-pentanedisulfonic acid, 2-aminoethanesulfonic acid, 4-hydroxybutane-1-sulfonic acid, and pharmaceutically acceptable salts thereof.

6. The method of claim 1, wherein the therapeutic compound is selected from the group consisting of 1-butanesulfonic acid, 1-decanesulfonic acid, 2-propanesulfonic acid, 3-pentanesulfonic acid, 4-heptanesulfonic acid, and pharmaceutically acceptable salts thereof.

7. The method of claim 1, wherein the therapeutic compound is 1,7-dihydroxy-4-heptanesulfonic acid, or a pharmaceutically acceptable salt thereof.

8. A method for inhibiting amyloid deposition in a subject comprising administering to the subject an effective amount of a therapeutic compound, the therapeutic compound comprising at least one sulfate group covalently attached to a carrier molecule; or a pharmaceutically acceptable salt thereof.

9. The method of claim 8, wherein the therapeutic compound is administered orally.

10. The method of claim 8, wherein the carrier molecule is selected from the group consisting of a polymer, a peptide, a peptidomimetic, an aliphatic group, an alicyclic group, a heterocyclic group, and combinations thereof.

11. The method of claim 10, wherein the carrier molecule is an aliphatic group.

12. The method of claim 8, wherein the therapeutic compound is selected from the group consisting of 2-hydroxymethyl-1,3-propanediol disulfate, 2-hydroxymethyl-2-methyl-1,3-propanediol disulfate, 1,3-cyclohexanediol disulfate, and pharmaceutically acceptable salts thereof.

13. The method of claim 8, wherein the therapeutic compound is 2,3,4,3',4'-sucrose pentasulfate, or a pharmaceutically acceptable salt thereof.

14. The method of claim 8, wherein the therapeutic compound is selected from the group consisting of 2-hydroxyethylsulfamic acid disulfate, 3-hydroxypropylsulfamic acid sulfate, and pharmaceutically acceptable salts thereof.

15. The method of claim 8, wherein the therapeutic compound is selected from the group consisting of 1,3,5,7-heptanetetraol tetrasulfate and 1,3,5,7,9-nonanepentaol pentasulfate, and pharmaceutically acceptable salts thereof.

16. The method of claim 1, wherein the carrier molecule comprises a targeting moiety.

17. The method of claim 8, wherein the carrier molecule comprises a targeting moiety.

18. A method for inhibiting amyloid deposition in a subject comprising administering to the subject an effective amount of a therapeutic compound, the therapeutic compound comprising at least one tetrazole group covalently attached to a carrier molecule, or a pharmaceutically acceptable salt thereof.

19. The method of claim 18, wherein the therapeutic compound is selected from the group consisting of 3-(1H-tetrazol-5-yl)-9H-thioxanthen-9-one 10,10-dioxide, 5,5-dithiobis(1-phenyltetrazole), 1H-tetrazole, 5-phenyl-1H-tetrazole, and 5-(2-aminoethanoic acid)-1H-tetrazole, and pharmaceutically acceptable salts thereof.

20. The method of claim 18, wherein the carrier molecule comprises a targeting moiety.

21. The method of claim 1, wherein the carrier molecule is selected from the group consisting of an aromatic group, a carbohydrate, and combinations thereof.

22. The method of claim 8, wherein the carrier molecule is selected from the group consisting of an aromatic group, a carbohydrate, and combinations thereof.

23. A method for inhibiting amyloid deposition in a subject comprising administering to the subject an effective amount of a therapeutic compound, or a pharmaceutically acceptable salt thereof, such that amyloid deposition is inhibited, the therapeutic compound having the formula:

$$Q-[-Y^-X^+]_n$$

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound;

wherein the carrier molecule comprises a targeting moiety.

24. The method of claim 23, wherein the therapeutic compound is administered orally.

25. The method of claim 23 further comprising administering the therapeutic compound in a pharmaceutically acceptable vehicle.

26. The method of claim 23, wherein the carrier molecule is selected from the group consisting of a polymer, a peptide, a peptidomimetic, an aliphatic group, an alicyclic group, a heterocyclic group, and combinations thereof.

27. The method of claim 23, wherein the carrier molecule is selected from the group consisting of an aromatic group, a carbohydrate, and combinations thereof.

28. The method of claim 23, wherein n is an integer between 1 and 10.

29. The method of claim 23, wherein the anionic group is selected from the group consisting of a sulfonate group, a sulfate group, a carboxylate group, a phosphate group, a phosphonate group,

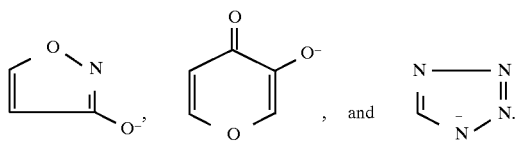

30. The method of claim 23, wherein the targeting moiety targets the therapeutic compound to the brain.

31. The method of claim 23, wherein the targeting moiety comprises an amino acid mimetic.

32. The method of claim 23, wherein the targeting moiety comprises a thyroxine mimetic.

33. The method of claim 23, wherein the targeting moiety allows transport of the therapeutic compound into cells by receptor-mediated endocytosis.

34. A method for inhibiting amyloid deposition in a subject comprising administering to the subject an effective amount of a prodrug, or a pharmaceutically acceptable salt thereof, wherein the prodrug is converted in vivo to a therapeutic compound, such that amyloid deposition is inhibited, the therapeutic compound having the formula:

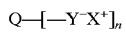

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound.

35. The method of claim 34, wherein the prodrug is administered orally.

36. The method of claim 34, further comprising administering the prodrug in a pharmaceutically acceptable vehicle.

37. The method of claim 34, wherein the carrier molecule is selected from the group consisting of a polymer, a peptide, a peptidomimetic, a carbohydrate, an aliphatic group, an alicyclic group, a heterocyclic group, and combinations thereof.

38. The method of claim 34, wherein the anionic group is selected from the group consisting of a sulfonate group, a sulfate group, a carboxylate group, a phosphate group, a phosphonate group,

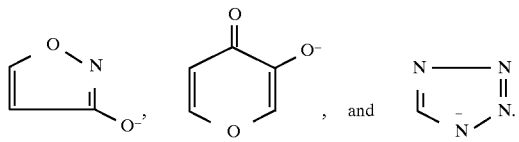

39. The method of claim 34, wherein the prodrug is an ester of a sulfate or a sulfonate.

40. The method of claim 39, wherein the prodrug is a cyclic ester.

41. The method of claim 39, wherein the prodrug is cleaved in vivo reductively or hydrolytically when the prodrug is administered to the subject.

42. The method of claim 34, wherein the carrier molecule comprises a targeting moiety.

43. The method of claim 42, wherein the targeting moiety targets the therapeutic compound to the brain.

44. The method of claim 42, wherein the targeting moiety comprises an amino acid mimetic.

45. The method of claim 42, wherein the targeting moiety comprises a thyroxine mimetic.

46. The method of claim 42, wherein the targeting moiety allows transport of the therapeutic compound into cells by receptor-mediated endocytosis.

47. A pharmaceutical composition for treating amyloidosis comprising a therapeutic compound, or a pharmaceutically acceptable salt thereof, in an amount sufficient to inhibit amyloid deposition in a subject, and a pharmaceutically acceptable vehicle, the therapeutic compound having the formula:

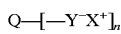

wherein $Y^-$ is an anionic group at physiological pH; Q is a carrier molecule; $X^+$ is a cationic group; and n is an integer selected such that the biodistribution of the therapeutic compound for an intended target site is not prevented while maintaining activity of the therapeutic compound;

wherein the carrier molecule comprises a targeting moiety.

48. The pharmaceutical composition of claim 47, wherein the carrier molecule is selected from the group consisting of a polymer, a peptide, a peptidomimetic, an aliphatic group, an alicyclic group, a heterocyclic group, and combinations thereof.

49. The pharmaceutical composition of claim 47, wherein the carrier molecule is selected from the group consisting of an aromatic group, a carbohydrate, and combinations thereof.

50. The pharmaceutical composition of claim 47, wherein n is an integer between 1 and 10.

51. The pharmaceutical composition of claim 47, wherein the anionic group is selected from the group consisting of a sulfonate group, a sulfate group, a carboxylate group, a phosphate group, a phosphonate group,

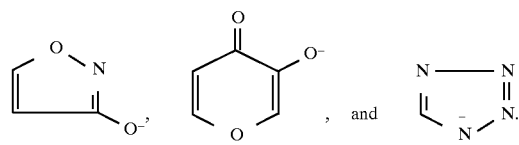

52. The pharmaceutical composition of claim 47, wherein the targeting moiety targets the therapeutic compound to the brain.

53. The pharmaceutical composition of claim 47, wherein the targeting moiety comprises an amino acid mimetic.

54. The pharmaceutical composition of claim 47, wherein the targeting moiety comprises a thyroxine mimetic.

55. The pharmaceutical composition of claim 47, wherein the targeting moiety allows transport of the therapeutic compound into cells by receptor-mediated endocytosis.

56. A pharmaceutical composition for inhibiting amyloid deposition in a subject comprising a prodrug, or a pharmaceutically acceptable salt thereof, in an amount sufficient to inhibit amyloid deposition in a subject, wherein the prodrug is converted in vivo to a therapeutic compound, the therapeutic compound having the formula:

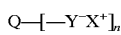

wherein Y⁻ is an anionic group at physiological pH; Q is a carrier molecule; X⁺ is a cationic group; and n is an integer selected such that the biodistribution of the therapeutic compound for an intended target site is not prevented while maintaining activity of the therapeutic compound;

and a pharmaceutically acceptable vehicle.

57. The pharmaceutical composition of claim 56, wherein the carrier molecule is selected from the group consisting of a polymer, a peptide, a peptidomimetic, a carbohydrate, an aliphatic group, an alicyclic group, a heterocyclic group, and combinations thereof.

58. The pharmaceutical composition of claim 56, wherein the anionic group is selected from the group consisting of a sulfonate group, a sulfate group, a carboxylate group, a phosphate group, a phosphonate group,

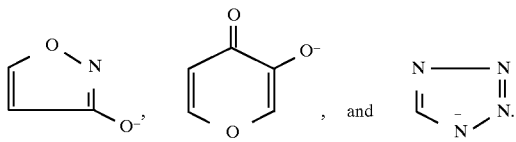

59. The pharmaceutical composition of claim 56, wherein the prodrug is an ester of a sulfate or a sulfonate.

60. The pharmaceutical composition of claim 59, wherein the prodrug is a cyclic ester.

61. The pharmaceutical composition of claim 56, wherein the prodrug is cleaved in vivo reductively or hydrolytically when the prodrug is administered to the subject.

62. The pharmaceutical composition of claim 56, wherein the carrier molecule comprises a targeting moiety.

63. The pharmaceutical composition of claim 62, wherein the targeting moiety targets the therapeutic compound to the brain.

64. The pharmaceutical composition of claim 62, wherein the targeting moiety comprises an amino acid mimetic.

65. The pharmaceutical composition of claim 62, wherein the targeting moiety comprises a thyroxine mimetic.

66. The pharmaceutical composition of claim 62, wherein the targeting moiety allows transport of the therapeutic compound into cells by receptor-mediated endocytosis.

* * * * *

UNITED STATES PATENT AND TRADEMARK OFFICE
CERTIFICATE OF CORRECTION

PATENT NO.    : 5,840,294 B1                                            Page 1 of 1
DATED         : November 24, 1998
INVENTOR(S)   : Kisilevsky et al.

It is certified that error appears in the above-identified patent and that said Letters Patent is hereby corrected as shown below:

Drawings,
Drawing Sheet 8, Figure 10, delete the following:

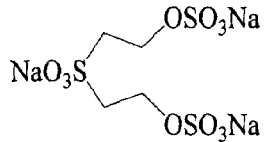

XXXII and insert therefor the following:

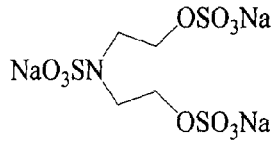

XXXII

Signed and Sealed this

Eighth Day of April, 2003

JAMES E. ROGAN
*Director of the United States Patent and Trademark Office*